United States Patent
Somers et al.

(10) Patent No.: US 10,621,882 B2
(45) Date of Patent: Apr. 14, 2020

(54) SYSTEM AND PROCESS FOR COGNITIVE ASSESSMENT AND TRAINING

(71) Applicants: TALI Health Pty Ltd, Melbourne (AU); Monash University, Clayton (AU)

(72) Inventors: Andrew Somers, Richmond (AU); Grace Lethlean, Richmond (AU); Hannah Kirk, Clayton (AU); Kim Cornish, Clayton (AU)

(73) Assignees: TALI Health Pty Ltd, Melbourne (AU); Monash University, Clayton (AU)

( * ) Notice: Subject to any disclaimer, the term of this patent is extended or adjusted under 35 U.S.C. 154(b) by 197 days.

(21) Appl. No.: 15/563,423

(22) PCT Filed: Mar. 31, 2015

(86) PCT No.: PCT/AU2015/050146
§ 371 (c)(1),
(2) Date: Sep. 29, 2017

(87) PCT Pub. No.: WO2016/154658
PCT Pub. Date: Oct. 6, 2016

(65) Prior Publication Data
US 2018/0090024 A1 Mar. 29, 2018

(51) Int. Cl.
*G09B 7/02* (2006.01)
*A63F 13/00* (2014.01)
(Continued)

(52) U.S. Cl.
CPC ............. *G09B 7/02* (2013.01); *A61B 5/168* (2013.01); *A63F 13/00* (2013.01); *A63F 13/44* (2014.09); *A63F 13/50* (2014.09)

(58) Field of Classification Search
CPC .................. A63F 13/00; G09B 7/02
See application file for complete search history.

(56) References Cited

U.S. PATENT DOCUMENTS

| 5,913,310 A | 6/1999 | Brown |
| 5,918,603 A * | 7/1999 | Brown .................. A63F 13/005 128/897 |

(Continued)

OTHER PUBLICATIONS

Extended European Search Report for Application No. 15886725.9, dated Sep. 10, 2018 (7 pages).

(Continued)

*Primary Examiner* — James S. McClellan
(74) *Attorney, Agent, or Firm* — Nixon Peabody LLP

(57) ABSTRACT

A process for cognitive assessment and training, the process being executed by at least one processor of a computing system and including the steps of: receiving interaction data representing interactions between an application executing on an electronic device and an individual interacting with the executing application; processing the interaction data to generate performance data representing quantitative measures of the performance of the individual with respect to the executing application; and processing the performance data for the individual to generate cognitive assessment data indicative of at least one attention-related ability of the individual.

19 Claims, 20 Drawing Sheets

(51) Int. Cl.
*A63F 13/44* (2014.01)
*A63F 13/50* (2014.01)
*A61B 5/16* (2006.01)

(56) References Cited

U.S. PATENT DOCUMENTS

| | | | | |
|---|---|---|---|---|
| 5,940,801 | A * | 8/1999 | Brown | G06F 19/322 |
| | | | | 273/429 |
| 2013/0101976 | A1* | 4/2013 | Roots | G09B 5/06 |
| | | | | 434/362 |
| 2013/0209977 | A1 | 8/2013 | Lathan | |
| 2014/0057244 | A1* | 2/2014 | Roots | G09B 7/00 |
| | | | | 434/362 |

OTHER PUBLICATIONS

International Search Report, PCT/AU2015/050146, dated May 1, 2015 (15 pages).
Written Opinion of International Searching Authority, PCT/AU2015/050146, dated May 1, 2015 (6 pages).

* cited by examiner (A)

(B)

SYSTEM AND PROCESS FOR COGNITIVE ASSESSMENT AND TRAINING

CROSS-REFERENCE TO RELATED APPLICATIONS

This application is a national stage of International Application No. PCT/AU2015/050146 filed on Mar. 31, 2015, and titled "System And Process For Cognitive Assessment And Training," which is herein incorporated by reference in its respective entirety.

TECHNICAL FIELD

The present invention relates to a system and process for assessing cognitive performance of individuals and for training individuals to improve their cognitive performance.

BACKGROUND

The reference to any prior art in this specification is not, and should not be taken as, an acknowledgment or any form of suggestion that the prior art forms part of the common general knowledge in Australia.

The diagnosis and treatment of developmental disabilities is an important problem faced by modern society. The diagnosis of developmental disabilities has increased significantly over the past decade, and executive function weaknesses, such as attention difficulties are a particularly common feature characterising the cognitive impairments of many affected individuals.

There is now widespread agreement that there are three core cognitive attentional processes that may be impaired in those with developmental disabilities, namely: i) selective attention, which determines the ability to selectively attend to aspects of the environment; ii) sustained attention, which enables the individual to focus on a task and to remain sensitive to incoming information; and iii) executive attention, relating to the ability to focus on a fixed goal while ignoring conflicting information. Difficulties in any one of these attentional processes in childhood have been shown to have detrimental effects on learning and social outcomes during school years and beyond. The degree of attention deficiency experienced by an individual will depend on the extent to which they are affected by a developmental disability, and on the presence of any other intellectual disabilities. Attention deficits are highly prevalent in a range of developmental disorders, including Autism Spectrum Disorders (ASDs), Down syndrome, Williams syndrome, and Fragile X syndrome.

The early diagnosis and treatment of attention deficiency is essential for several reasons. First, it may lead to improved educational and social opportunities, and therefore to a better quality of life, for individuals affected by developmental disabilities. There are several difficulties with current approaches to assessing developmental disabilities. In particular, there is a general lack of objective methods for assessment, which typically involves the subjective assessment of an individual's state of affliction by a medical health professional. These assessments are difficult to repeat frequently, and each assessment requires a consultation with the medical professional. Although these behavioural ratings are informative, alone they are not sufficient because attention difficulties can stem from a number of underlying cognitive weaknesses. For instance several children with developmental disabilities share common profiles of inattention and hyperactivity, yet syndrome specific cognitive attention profiles have been shown. Therefore relying on purely behavioural ratings may result in overlooking core cognitive difficulties.

Traditionally, treatment for developmental disabilities has been implemented in the form of pharmaceutical intervention. However, this type of treatment has the disadvantage of being limited in its ability to accommodate for differences in attention impairment for individuals who suffer from other intellectual disabilities, and may be unsuitable for patients who have adverse reactions to the medications. Pharmaceutical interventions also only target behavioural weaknesses, and although psychostimulant medication has been shown to be effective in typically developing children in the short term, the long term effects of this intervention are not known.

The traditional approaches to diagnosing and treating developmental disabilities of an individual in isolation are also problematic. These methods involving case-by-case assessments are inadequate to effectively deal with the growing issue of childhood developmental disability at a national or global scale.

It is desired to provide a system and process that alleviate one or more difficulties of the prior art, or to at least provide a useful alternative.

SUMMARY

In accordance with some embodiments of the present invention, there is provided a process for cognitive assessment and training, the process being executed by at least one processor of a computing system, and including the steps of:
  receiving interaction data representing interactions between an application executing on an electronic device and an individual interacting with the executing application;
  processing the interaction data to generate performance data representing quantitative measures of the performance of the individual with respect to the executing application; and
  processing the performance data for the individual to generate cognitive assessment data indicative of at least one attention-related ability of the individual.

In some embodiments, the application is a game, and the interaction data represents interactions between the game and the individual playing the game, the game being configured to assess attention-related abilities of the individual.

In some embodiments, the quantitative measures of the performance of the individual with respect to the executing application include quantitative measures of accuracy, error rate, and response time.

In some embodiments, the step of processing the performance data includes performing multivariate analysis of the quantitative measures to generate the cognitive assessment data.

In some embodiments, the multivariate analysis includes at least one of a principal component analysis and a clustering process.

In some embodiments, the step of processing the performance data includes processing the performance data for the individual and corresponding performance data for one or more other individuals having one or more cognitive ability classifications, including a neurotypical classification and/or one or more developmental disability classifications, the cognitive assessment data being indicative of a classification of the individual with respect to the one or more cognitive ability classifications.

In some embodiments, the process includes generating display data representing a visualisation of the cognitive assessment data of the individual and the one or more cognitive ability classifications of the one or more other individuals.

In some embodiments, the process includes generating display data representing a visualisation of one or more of the quantitative measures of performance of the individual and one or more corresponding quantitative measures of performance for one or more other individuals to allow a user viewing the visualisation to compare the performance of the individual to the corresponding performance of the other individuals.

In some embodiments, the visualisation includes an interactive control for selecting the one or more quantitative measures of performance for display to the user.

In some embodiments, the one or more other individuals have one or more cognitive ability classifications selected by a user from a set of cognitive ability classifications.

In some embodiments, the visualisation is configured to visually differentiate any quantitative measures of performance of the individual that differ significantly from the corresponding quantitative measures of performance for the other individuals.

In accordance with some embodiments of the present invention, there is provided a process for assessing and training cognitive performance of an individual, the process being executed by at least one processor of a computing system and including:
 displaying a plurality of visual stimuli on a display of the computing system;
 receiving inputs of an individual using the computing system, the inputs being responsive to the displayed visual stimuli;
 generating interaction data representing the visual stimuli and the corresponding inputs of the individual; and
 sending the interaction data to a data processing system configured to process the interaction data to generate performance data representing quantitative measures of the performance of the individual with respect to the visual stimuli.

The computing system may be a tablet computing device (e.g., an iPad) or a smartphone.

In accordance with some embodiments of the present invention, there is provided a process for assessing and training cognitive performance of an individual, the process being executed by at least one processor of a computing system and including:
 displaying a plurality of visual stimuli on a display of the computing system;
 receiving inputs of an individual using the computing system responsive to the displayed visual stimuli;
 generating interaction data representing the visual stimuli and the corresponding inputs of the individual; and
 processing the interaction data to generate performance data representing quantitative measures of the performance of the individual with respect to the visual stimuli.

In some embodiments, the visual stimuli represent a game being played by the individual, the visual stimuli being configured for assessing and training attention-related abilities of the individual.

In accordance with some embodiments of the present invention, there is provided a computer program product for cognitive assessment and training of an individual, including executable instructions that, when executed by at least one processor of a computing system, performs any one of the above processes.

In accordance with some embodiments of the present invention, there is provided a cognitive assessment and training system, including:
 a random access memory;
 at least one processor;
 a display to display application content to a user of the system;
 at least one input device to receive input from the individual;
 wherein the system is configured to execute any one of the above processes.

In some embodiments, the system is a tablet computer and the display and input device are components of a touchscreen of the tablet computer.

In accordance with some embodiments of the present invention, there is provided a system for cognitive assessment and training, including:
 a data receiving component configured to receive interaction data representing interactions between an application executing on an electronic device and an individual interacting with the executing application;
 a statistical processing component configured to process the interaction data to generate performance data representing quantitative measures of the performance of the individual with respect to the executing application; and
 a classification component configured to process the performance data for the individual to generate classification data indicative of at least one developmental disability classification for the individual.

In accordance with some embodiments of the present invention, there is provided a method for cognitive assessment and training of an individual, including:
 providing cognitive training sessions in which the individual continuously interacts with a cognitive assessment and training system for at least a predetermined period of time, the cognitive assessment and training system being configured to execute any one of the above processes, wherein the executing process implements a computer game being played by the individual, and the computer game is configured to train attention-related abilities of the individual playing the game; and
 the step of processing the interaction data is performed at least before and after the cognitive training sessions to assess improvements in one or more of the attention-related abilities of the individual.

BRIEF DESCRIPTION OF THE DRAWINGS

Some embodiments of the present invention are hereafter described, by way of non-limiting example only, with reference to the accompanying drawing in which.

DETAILED DESCRIPTION

Figure 1:
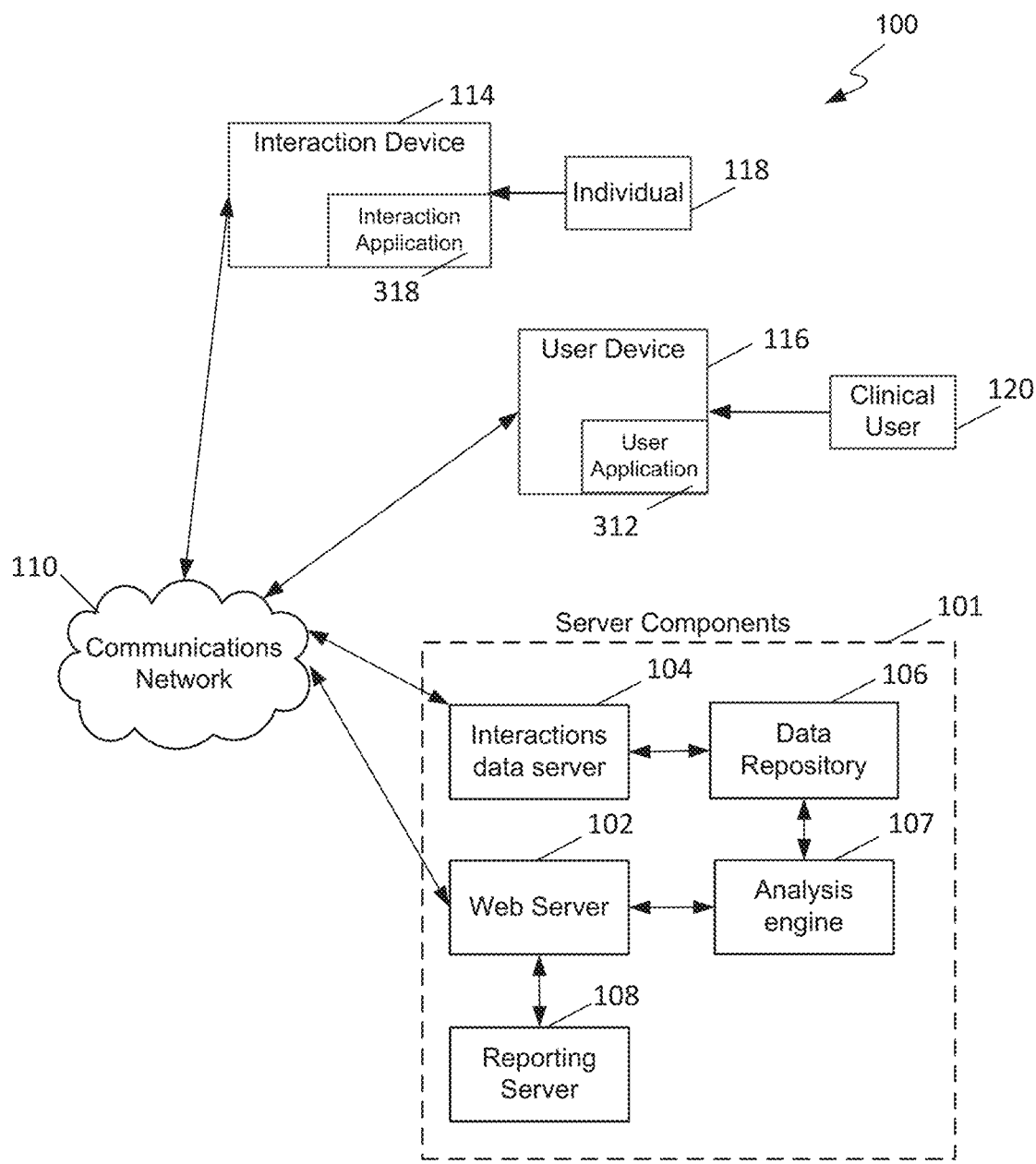
FIG. 1 is a schematic diagram of a cognitive assessment and training system in accordance with an embodiment of the present invention.

The described embodiments of the present invention include a cognitive assessment and training system and process that objectively determine quantitative measures of cognitive performance of individuals of both typical and atypical cognitive abilities by non-invasively measuring each individual's interactions with a cognitive assessment and training application (e.g., a game) executing on an electronic device (typically, a tablet computer), referred to hereinafter for convenience of description as an "interaction device". An individual's responses to stimuli provided by the cognitive assessment and training application are captured and processed to generate corresponding quantitative measures of the individual's cognitive performance, and to generate classification data indicative of at least one cognitive classification for the individual.

The described system and process provide an assessment of the cognitive performance of the individual based on their interaction performance, and can employ various types of analysis to produce a variety of quantitative performance measures for the individual. The cognitive performance summary of the individual can be stored by the system, and the assessment repeated over time in order to provide a record of any changes in the performance of the individual over time, for example in response to treatment. A medical practitioner or researcher can view the individual's stored cognitive performance for the purpose of making a diagnosis, or to track their progress, for example.

The cognitive assessment and training system and process can be applied to generate cognitive performance data for a plurality of individuals afflicted by potentially distinct developmental disabilities and/or intellectual disability conditions, allowing comparative analysis between the cognitive performance of individuals based on their developmental condition or any of a number of other traits, such as age, gender, and/or length of treatment, for example. Medical practitioners and clinical researchers can utilise the performance data generated by the system to model cognitive conditions in order to further improve diagnosis and treatment for individuals affected by developmental disorders.

As described below, the cognitive assessment and training system and process described herein provide customisation options that allow clinical users to modify the analysis methods in response to visualisations of the cognitive ability data, for example by eliminating redundant parameters.

Although embodiments of the present invention are generally described herein in the context of individuals interacting with cognitive assessment and training applications in the form of electronic games, other types of cognitive assessment and training applications could be used in other embodiments, providing other forms of stimulus and measuring responses thereto. However, the use of electronic games promotes engagement of the individual to be assessed, and is particularly advantageous in the assessment and treatment of children. As described below, the cognitive game applications allow quantitative evaluation of specific cognitive functions of the individual. This allows a clinical medical professional to implement a diagnosis and treatment program based on the specific needs of the individual, as indicated by the cognitive performance data generated by the cognitive assessment system and process.

In the described embodiments, the cognitive performance of an individual is assessed with respect to the attention executive function of that individual. That is, the interaction devices execute applications that present situations conducive to measuring an individual's selective, sustained and/or controlled attention based on the individual's measured responses to those situations or stimuli. However, it will be apparent to those skilled in the art that the described processes can be readily applied to the assessment of other measurable cognitive functions, such as for example socialisation and working memory executive functions.

Although the embodiments described herein utilise electronic games, it will be apparent to the skilled addressee that other types of electronic applications can be used to obtain responses representative of an individual's cognitive attention capabilities. For example, measurements of cognitive attention response can be obtained from an individual engaging in a concentration related task wherein the interactive situations or stimuli are not presented in the context of a game environment.

The cognitive assessment and training system and process allow medical practitioners, researchers, and carers to quantitatively compare the cognitive functions of an individual to other individuals with similar or related developmental disabilities for the purposes of improving treatment and/or diagnosis, allowing accurate identification of trends in the treatment and severity of the disabilities, and enabling improved research outcomes by providing a large collection of clinical data. Additionally, the system and process are also effective at training individuals to improve attention-related aspects of their cognitive abilities, as described below, and these improvements have been shown to remain up to at least 3 months after use of the cognitive assessment and training system and process had ceased.

The cognitive assessment and training system and process described herein:

1) non-invasively collect interaction data representing an individual's interactions with an electronic application (e.g., game);
2) process the interaction data to generate performance data representing quantitative measures of the individual's performance with respect to the application;
3) process the performance data for the first individual to generate classification data indicative of at least one developmental disability classification for the first individual; this can be used to identify developmental disabilities and related disorders affecting the individual based on a comparison of their assessed performance to the corresponding performance of other individuals with known assessments of developmental disabilities or related disorders, and to evaluate the cognitive performance of the individual over time;
4) generate reports summarising the performance of an individual; and
5) Visually display the performance data of selected individuals to clinical users to enable modification of the performance determination means.

As shown in FIG. 1, a cognitive assessment and training system 100 includes client devices 114, 116, and server components 101. The client devices include at least one interaction device 114 for use by an individual 118 suffering from a developmental disability, and one or more user devices 116 for use by at least one user 120, who may be a clinical user such as a medical professional providing diagnosis or treatment to the individual 118, or a researcher.

The interaction 114 and user 116 devices communicate with the server components 101 over a communications network 110 such as the Internet. In the described embodiment, the server components 101 include a web server 102, which provides a user interface for system access, an interaction data server 104 which receives interaction data from the interaction device 114, and stores it in an associated data repository 106, an analysis engine 107 which analyse the received interaction data, and a reporting server 108 which generates cognitive performance data and reports based on the analysis performed by the analysis engine 107.

Figure 2:
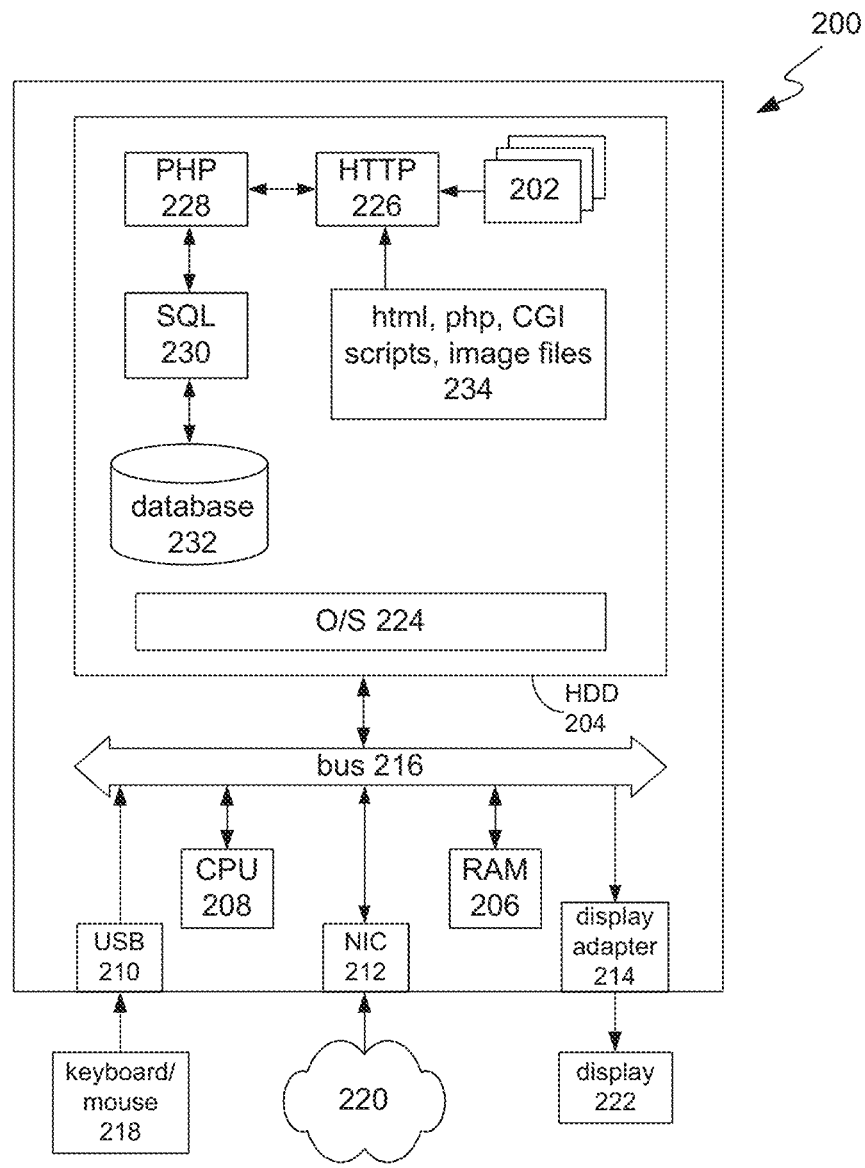
FIG. 2 is a block diagram of a computer system used to implement the user device, interaction device and/or the server devices of the cognitive assessment and training system in the described embodiments.

In the described embodiment, each of the server components 101 is a standard computer system such as an Intel Architecture IA-32 based computer system 2, as shown in FIG. 2, and the processes executed by the system 100 are implemented as programming instructions of one or more software modules stored on non-volatile (e.g., hard disk or solid-state drive) storage 204 associated with the corresponding computer system, as shown in FIG. 2. However, it will be apparent that at least some of the steps of any of the described processes could alternatively be implemented, either in part or in its entirety, as one or more dedicated hardware components, such as gate configuration data for one or more field programmable gate arrays (FPGAs), or as application-specific integrated circuits (ASICs), for example. It will also be apparent to those skilled in the art that in other embodiments the various components of the cognitive assessment system 100 may be distributed or combined in a variety of alternative ways other than those described herein, and at different locations.

Each computer system includes standard computer components, including random access memory (RAM) 206, at least one processor 208, and external interfaces 210, 212, 214, interconnected by at least one bus 216. The external interfaces include a wireless network interface connector (NIC) 212 which connects the system 100 to the communications network 220, and a display adapter 214, which may be connected to a display device such as an LCD panel display 222, which may be a touchscreen panel display. Depending on the specific type of computer system, the external interfaces may also include universal serial bus (USB) interfaces 210, at least one of which may be connected to a keyboard 218 and a pointing device such as a mouse 619.

Each computer system may also include a number of standard software modules 226 to 230, including an operating system 224 such as Linux or Microsoft Windows. The web server 102 includes web server software 226 such as Apache, available at http://www.apache.org, and scripting language support 228 such as PHP, available at http://www.php.net, or Microsoft ASP. The data repository 106 includes a structured query language (SQL) database, and an SQL interface 230 such as MySQL, available from http://www.mysql.com, which allows data to be stored in and retrieved from the SQL database.

Figure 3:
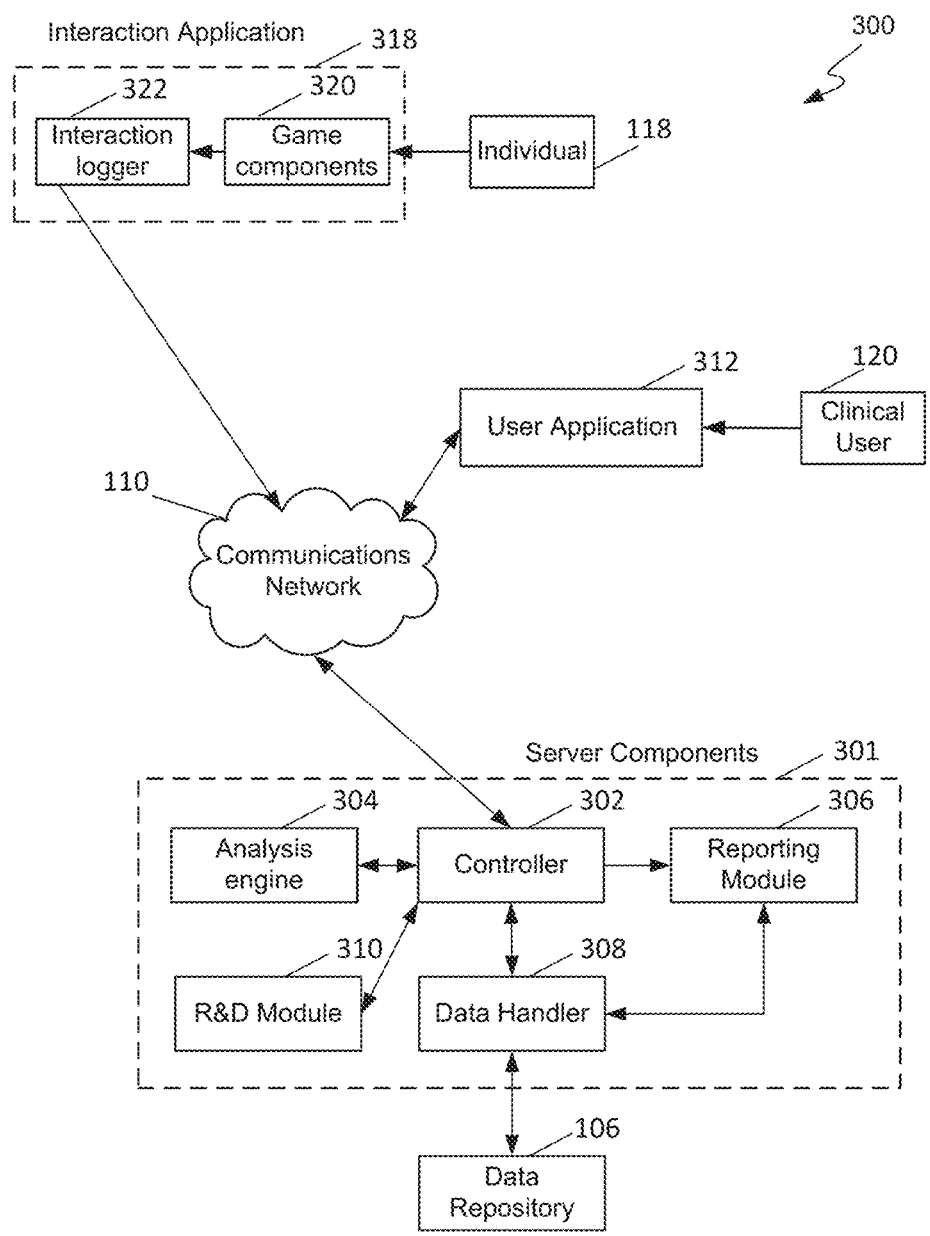
FIG. 3 is a schematic diagram of the functional components of the cognitive assessment and training system.

FIG. 3 is a block diagram of the functional components of the cognitive assessment system 100. An interaction application (also referred to herein after for convenience as a "game") 318 is executed on the interaction device 114 for the purpose of obtaining responses of the individual 118 to stimuli or situations. In the described embodiments, the interaction device 114 is a standard tablet, laptop or other portable computing device capable of executing a game application 318, and typically includes a touchscreen display panel to receive inputs from the individual in response to stimuli displayed on the screen of the portable computing device. The game 318 presents stimuli or situations to the individual in the form of game scenarios generated by the game components or code 320, and receives input in response to those stimuli from the individual 118. An interaction logging component or logger 322 timestamps and logs the stimuli and corresponding responses, and sends the resulting interaction data to the interaction data server 104 for storage, as described below.

The user devices 116 execute at least one user application 312 to access the server components 101 in order to perform analyses of the interaction data stored in the data repository and to generate corresponding reports for individuals assessed by the system 100. In the described embodiment, the user application 312 is a standard web browser application such as Google Chrome or Microsoft Internet Explorer. However, in other embodiments the user application 312 may be, for example, a dedicated application that allows the exchange of data between the user devices 116 and the server components 101 over a secure communications channel, and is able to display information received from the server components 101 to the clinical user or researcher 120.

The web server 302 provides a single point of entry for a remote user 120 to perform functions including: i) transforming and analysing the interaction data received from the interaction device 114 to produce a quantitative assessment of cognitive performance via the analysis engine 304; ii) storing and retrieving cognitive performance data in and from the data repository 106; and iii) outputting the determined cognitive performance measures in the form of a report via the reporting module 306.

The data repository 106 stores analysis data, including models or representations of the cognitive performance of each assessed individual, and of general cognitive disability conditions recognised by the system. The R&D ("research and development") module 310 allows clinical users 120 to create models for new cognitive disability conditions and to modify existing condition models based on the data collected from an assessed individual 118 with an a priori diagnosis, as described below.

For example, when comparing the performance metrics of at least one individual to one or more reference data sets for other individuals having respective cognitive classifications, each reference data set can be selected and customised to select aspects of interest or to exclude extraneous data; for example, a reference data set can be selected to include performance metrics for all 4 year old individuals assessed by the system 100, all male individuals, or any combination of these or other characteristics. The clinical user or researcher 120 can then select a number of data variables to use for comparison between the individual to be assessed and the selected reference data. Although the clinical user or researcher 120 can build these models to look for new cognitive conditions or classifications, a particularly useful feature of the system 100 is to provide a quantitative measure indicative of where an assessed individual sits on the ASD spectrum.

Reporting data is stored within a report database 510, including the parameters of the assessed individual's performance model over selectable time periods, and clinical notes applied by the practitioner. In the described embodiment, the report storage means 510 is linked to the R&D module 310, allowing the clinical users to modify the format and content of the report based on developments in the field.

Figure 4:
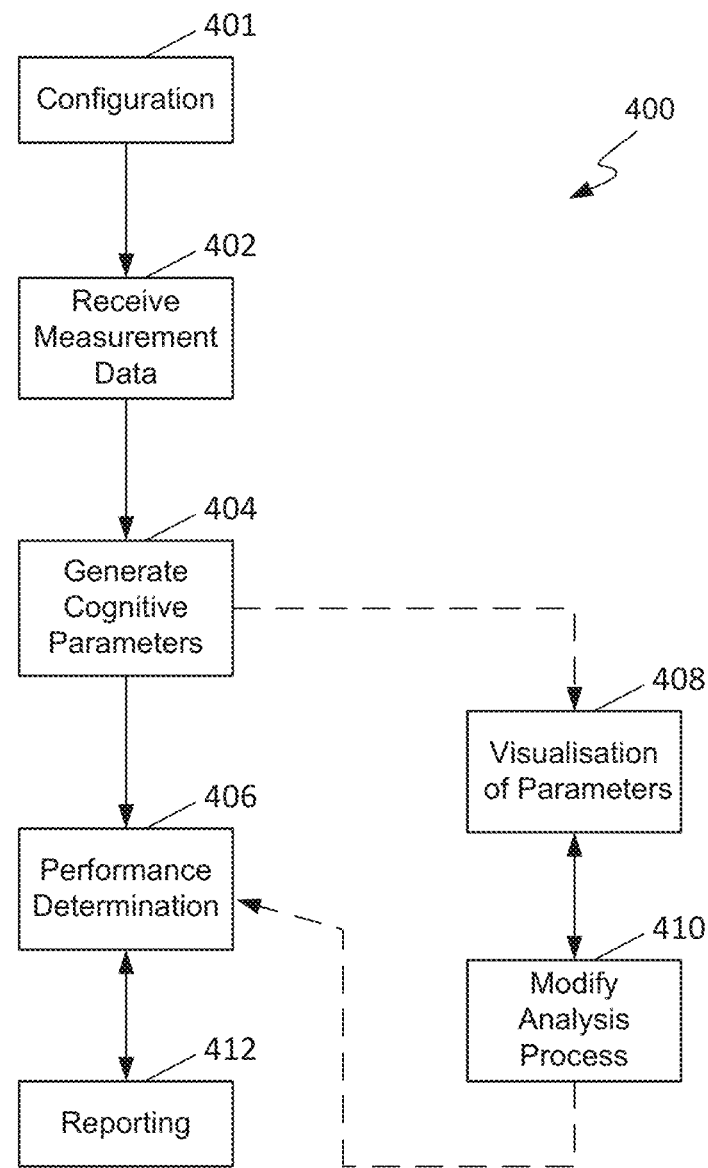
FIG. 4 is a flow diagram of a cognitive assessment process executed by the cognitive assessment system in accordance with an embodiment of the present invention.
Figure 5:
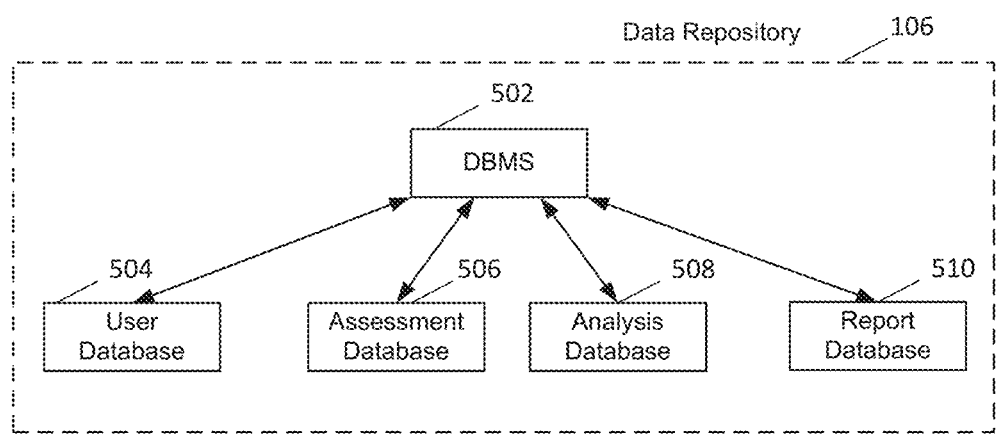
FIG. 5 is a schematic diagram of a data storage and management component of the cognitive assessment and training system.

FIG. 4 is a flow diagram of a cognitive assessment process 400 executed by the server components 101. Configuration steps 401 are performed to register individuals to be assessed 118, clinical users 120, and game application information. An individual to be assessed interacts with the game application 318 (by playing the game), and the interaction logger 322 sends the resulting interaction data to the interaction data server 104, which stores the received interaction data in an interaction data table 506 of the data repository 106.

At step 404, the analysis engine 304 processes the received interaction data to generate performance data representing statistics on various quantitative measures or metrics of the individual's performance during their interaction with the game application 318. In the described embodiments, these metrics are selected from a set of metrics that typically includes measures of accuracy, error rate, response time, response erraticness (defined as the average angle between lines joining successive input (e.g., touch) locations), the total number of inputs (e.g., touches), the total game time, the number of game levels played, the highest game level achieved, the number of level attempts, and game progress (measured as the difference between the starting level and the finishing level of a game played during a session); however, it will be apparent to those skilled in the art that other performance metrics may be used in other embodiments, either in addition to, or instead of, any of these metrics.

At step 406, the performance data is processed to generate classification data indicative of at least one developmental disability classification for the individual.

At step 412, the system 100 reports the determined performance data of an individual 412 to one or more users via the reporting module 306. The performance determination 406 and reporting 412 steps can be automatically scheduled by the system 100 such that an individual's progress is tracked in association with a treatment program or otherwise. In any case, a clinical user 120 with appropriate authority can request an update of the cognitive performance of an individual and/or the generation of a performance report at any time.

Optionally, a clinical user 120 can cause the analysis engine 304 to generate display data to allow the clinical user 120 to visualise the generated cognitive performance parameters for one or more assessed individuals 408 on a display associated with the user device 116. Based on the visualisation, at step 410 the clinical user 120 can optionally modify the analysis process by which the analysis engine 304 determines the cognitive performance or classifications of assessed individuals. As described below, this general process can be iterative, allowing a clinician 120 to repeatedly display, filter, transform and modify parameters that influence the cognitive performance or classification(s) of one or more individuals as determined by the system.

Figure 6:
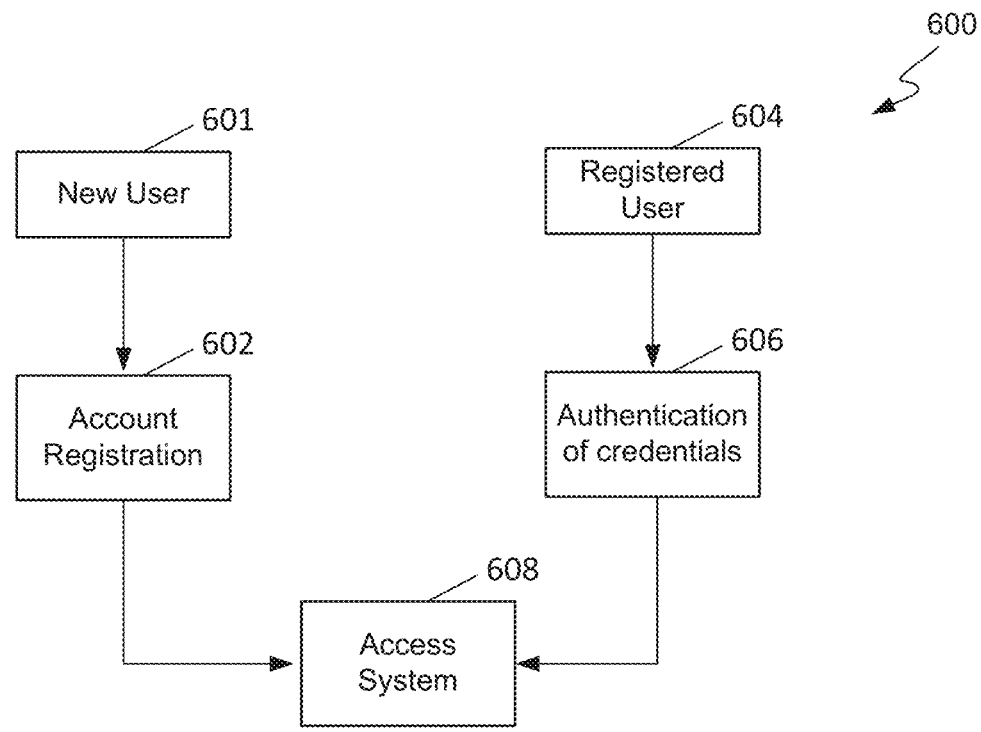
FIG. 6 is a flow diagram of an authorisation process by which users register with and are authenticated to access the cognitive assessment and training system.
Figure 7:
FIG. 7 is a screenshot of a user login screen of the cognitive assessment and training system.

In order to use the cognitive assessment system 100, a user first registers with the system 100. FIG. 6 illustrates a user registration process 600 by which a new user 601 becomes recognised as a registered user 604 within the system 100 following account registration 606. Account registration 602 involves the new user 601 choosing a user name and/or password combination which becomes associated with that user 601 for future logins to the system 100. Different types of user are recognised by the system 100, including individuals to be assessed 118 and clinicians who may be further categorised based on their role and level of access to the system data. To log into the system 100, a registered user 604 enters their username and password into textboxes of a login screen, as shown in FIG. 7, for authentication by the system 100 at step 606, involving a verification of user identifiable information (such as username and password) against the recorded details associated with the user in the user database 504 of the data repository 106.

Figure 8:
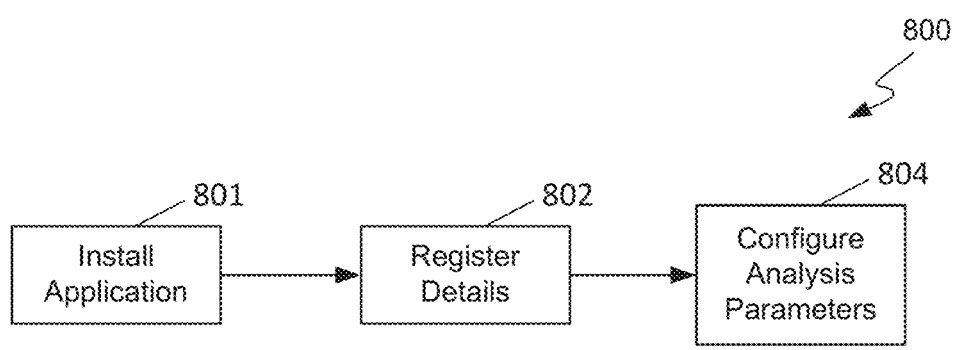
FIG. 8 is a flow diagram of a game installation and registration process executed by the cognitive assessment and training system.

As shown in FIG. 8, configuration of the cognitive assessment system 401 includes the installation of a game application 318 of the system 100 on an interaction device 114 at step 801. This is typically achieved by copying the game application 318 from physical media, such as a CD, DVD-ROM, or removable storage device (for example a USB key) to create a local copy of the game application 318 on the interaction device 114. Alternatively, the interaction device 114 may obtain the game application 318 via communication with an external game server (not shown) of the system 100 over a communications network, which may be the communications network 110 shown in FIG. 1.

Once installed, the game application 318 can be executed on the interaction device 114 in the usual way. For example, if the interaction device 114 is an Apple iPad, then at step 901 the game application 318 is executed by tapping a graphical icon representing the game application 318 on the touchscreen display of the interaction device 114.

Figure 9:
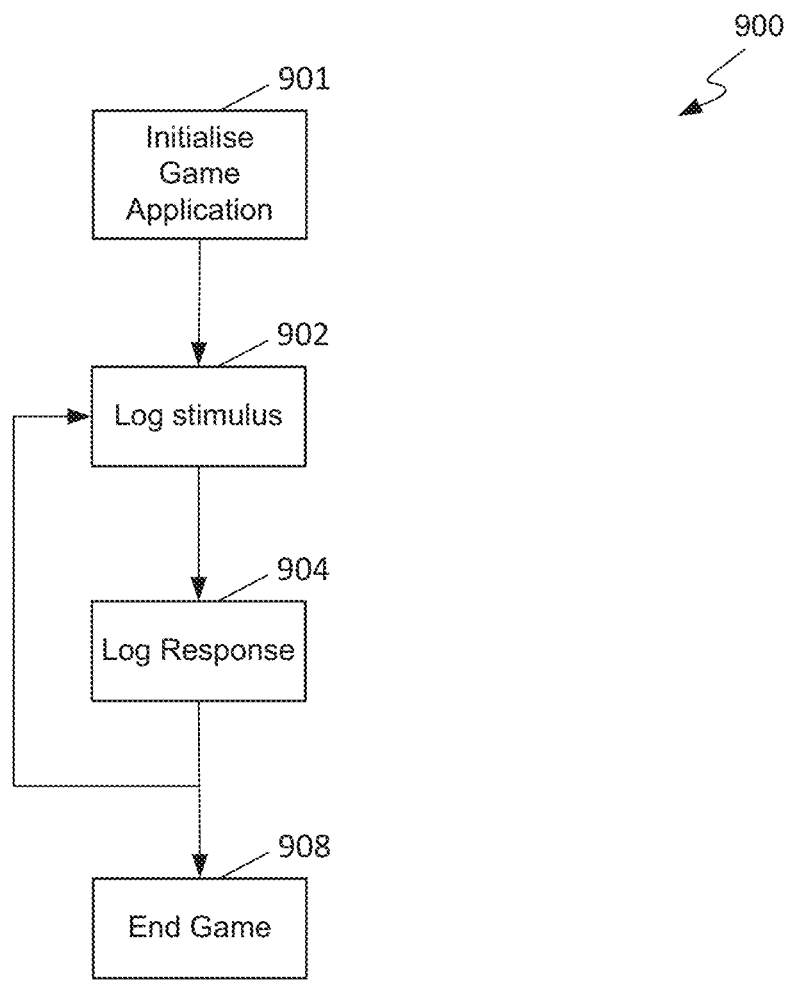
FIG. 9 is a flow diagram of a process of the cognitive assessment process of FIG. 4 for generating interaction data.

An individual to be assessed 118 interacts with the game application 318 by simply playing the game implemented by the game application 318 on the interaction device 114. During gameplay, the game application 318 presents the individual 118 with a sequence of game situations or stimuli, each prompting a response from the individual. The interaction data is generated by the interaction logger 322 logging each stimulus presented to the individual at step 902, and the corresponding response of the individual at step 904, as shown in FIG. 9, until game termination at step 908.

In the described embodiment, these events are logged by including a corresponding logging instructions in the high-level programming language instructions of each game. However, it will be apparent to those skilled in the art that these logging events may alternatively be included in a library that includes subroutines or functions referenced by the high-level programming instructions of the game, which can be used to convert games that were not specifically programmed for use with the system 100 two nevertheless be used with the system 100 as described herein.

The resulting interaction data is transmitted to the interaction data server 104 via the communications network 110, and the interaction data server 104 stores the received interaction data in an assessment table 506 of the data repository 106. In the described embodiment, the interaction logger 322 stores the interaction data locally until game termination, at which point the interaction logger 322 sends all of the interaction data for that game session to the interaction data server 104. However, in other embodiments of the interaction logger 322 may send the interaction data during gameplay.

The interaction data for a game session includes information identifying which game object was touched by the individual, when it was touched, how was touched (e.g., whether the individual's finger was moved during a touch event, and whether multiple fingers were used), and what was displayed on the screen at that time. In the described embodiment, the interaction data is in an XML format, although this need not be the case in other embodiments. An excerpt of an XML interaction data file is shown below.

```
<?xml version="1.0" encoding="utf-8"?>
<trial time="17/06/2014 11:26:46 AM">
    <screensize>(1024, 720)</screensize>
    <mascot>Mascot_Pirate</mascot>
    <trackerdata>
        <level>1.0</level>
        <action>
            <time>10.05</time>
            <touchonposition>(289, 75)</touchonposition>
            <touchoffposition>(289, 75)</touchoffposition>
            <touchduration>107</touchduration>
            <touchtype>TargetFish</touchtype>
            <fishtype>GoldFish</fishtype>
            <fishposition>(312, 77)</fishposition>
        </action>
        <action>
            <time>14.65</time>
            <touchonposition>(485, 287)</touchonposition>
            <touchoffposition>(485, 287)</touchoffposition>
            <touchduration>153</touchduration>
            <touchtype>InvalidTouch</touchtype>
        </action>
        ...
        <remainingfish>
            <fishtype>GoldFish</fishtype>
            <fishposition>(881, 619)</fishposition>
        </remainingfish>
        <levelcomplete>yes</levelcomplete>
        <totaltouchcount>7</totaltouchcount>
        <fishcorrect>6</fishcorrect>
        <fishincorrect>1</fishincorrect>
    </trackerdata>
    <trackerdata>
        <level>2.0</level>
        <action>
            ...
        </trackerdata>
</trial>
```

Figure 19:
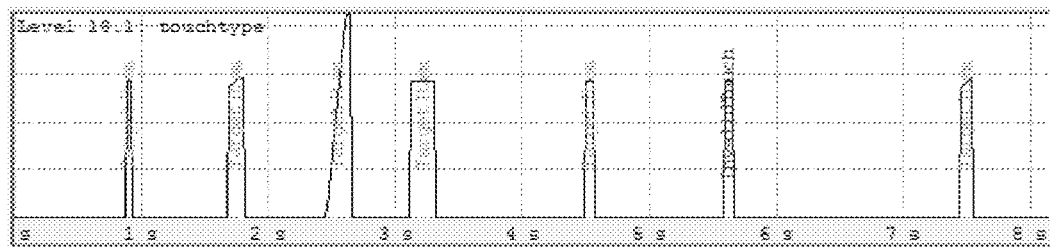
FIG. 19 is a partial screenshot of a graphical representation of touch events as a function of time during gameplay, representing the individual's touchscreen inputs with labels indicating classifications of those inputs.

As will be apparent from the XML excerpt, the interaction data includes, inter alia, data identifying the level numbers being played, and within each level, the screen coordinates of each game object (in this example, a TargetFish object), the screen coordinates of each screen touch event by the individual being assessed (including the start and end points of each touch event), the temporal duration of each touch event, and timestamps for the display of each object and the start time of the corresponding touch event. If desired, these individual events can be visualised graphically by the system 100, as shown in FIG. 19.

Transmission occurs via the communications network 110 using a transport layer protocol such as TCP/IP. To transmit the interaction data, the interaction device 114 may utilise a wireless networking interface operable in accordance with an IEEE 802.11 or "WiFi" wireless communications protocol to relay the data to the data server 104 via a local wireless network. Alternatively, the interaction device 114 can be connected to a routing or gateway node of the communications network 110 via a direct physical connection, where data transmission occurs to the network 110 via an Ethernet IEEE 802.3 protocol.

The selection of a game to use in the assessment of a particular individual 118 may be based on factors relevant to the individual's condition, or the specific developmental disability that the treating medical practitioner wishes to test for. In the described embodiment, the game applications 318 provided with the cognitive assessment system 100 include game applications that allow clinicians to test for a variety of developmental disabilities and other intellectual disabilities via the assessment of different types of attention executive functions.

In general, each game application 318 provides a fixed linear hierarchy of successive game levels so that each individual playing a game progresses through the same levels in the same order, the only exception being that each level needs to be 'passed' before succeeding to the next higher level in the hierarchy. If a level is not passed, then it needs to be repeated before the individual can progress to the next level.

Figure 10:
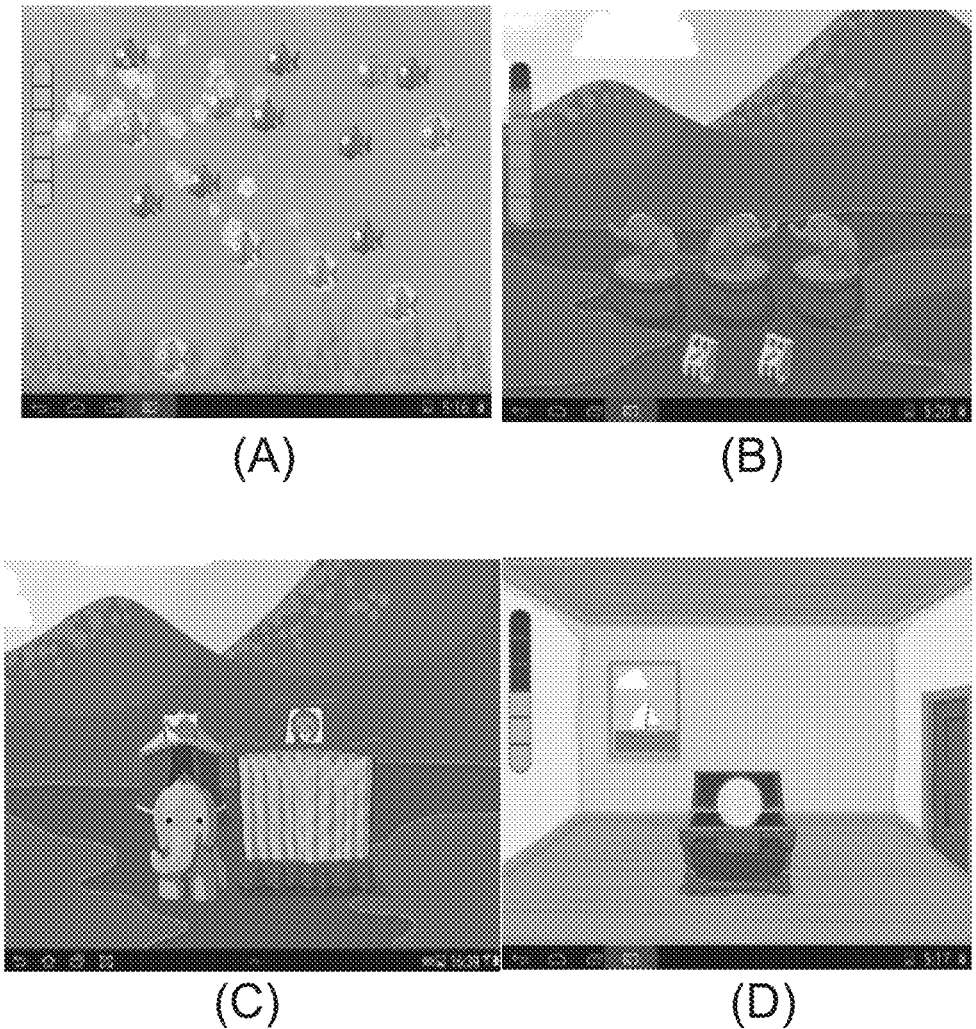
FIGS. 10A to 10D are screenshots of game applications of the cognitive assessment and training system.

Some games measure selective attention by challenging the individual 118 to differentiate objects based on criteria such as colour and size. A deficiency in this cognitive ability is associated with autism spectrum disorders. An example of a game that uses differentiation to measure selective attention is the 'Find a fish' game, a screenshot of which is shown in FIG. 10a.

In the 'Find a fish' game, target fish remain constant throughout all trials and are always orange in colour and medium in size. There are a total of 8 target fish per trial, and the individual 118 is required to find 6 of these 8 fish in order to successfully complete each level. Distractors vary in frequency and dimension as the levels progress. There are either: None, Some (4), Many (8) or Lots (16) of distractors, and their numbers vary in the proportion that they are similar to the target (0%, 25%, 50%, 75% & 100%). The first dimension that the distractors vary on is colour. The second dimension that the distractors vary on is size. In later trials they vary on both size and colour.

If the individual being assessed does not press anything for 15 seconds, or if 3 consecutive errors are made, then bubbles appear at the side of the screen to prompt a response from the individual. If nothing is pressed after 30 seconds, or if 3 consecutive errors are made again at any point throughout the trial, then the avatar's head pops into view from the side of the screen and holds up a sign showing the correct demonstration (finger touching the target fish).

Attentional control is measured by a different type of game, such as a type of Attention Network Test that measures conflict resolution and resistance to distractor inhibition. Examples are the 'Feed Elvis' and 'Sleepy Elvis' games shown in FIGS. 10b and 10c.

The 'Feed Elvis' game requires that the individual 118 determine the direction of a target, and make a selection that resolves a problem. The target is Elvis the elephant (central target). Individuals must orient their attention to Elvis and then respond appropriately based on his orientation. If Elvis's trunk is pointing to the right, then the child is required to select the right peanut bag. Distractors are elephants that are the same as Elvis, and act as flankers. They appear next to Elvis and increase in frequency from 2 to 4 flankers. In addition, they also differ in size from Elvis as well as space. Importantly, the direction that the flankers face also varies with the flankers either facing the same direction as Elvis (congruent) or the opposite direction (incongruent). Incongruent trials are deemed to be harder, because the child has to overrule the direction that the majority of the elephants are facing and respond only to the direction that Elvis (central target) is facing.

If on any trials, including the practice trials, the child is inactive for 15 seconds then a green arrow comes down and points to Elvis in the middle. If the individual presses other items on the screen other than the bags more than 15 times, then the two bags glow green. If either of these occur twice in a row, then the avatar demonstrates the correct response.

In 'Sleepy Elvis' the individual 118 is instructed that they have to respond as quickly as possible by pressing a target (Elvis the elephant), and to inhibit a response when a no-go stimulus is presented (lion). This game primarily gets harder by reducing the display time of the target and the inter-stimulus interval (ISI), being the time between the display of successive stimuli. In the hardest levels, distractions occur as the lion begins to disguise himself as Elvis. These trials incorporate complex aspects of inhibition, and are closely related to stop signal tasks. Individuals are likely to begin making a response when the lion looks like Elvis, however they have to inhibit this response when the disguise falls off. These is a harder task as a motor response has already begun.

If Elvis is not pressed in the given time limit, then verbal instructions occur voice over states 'Press Elvis as quickly as you can!' If the individual still does not press the target, then the avatar demonstrates the correct response.

Sustained attention can be tested by games that assess cognitive 'focus'. An example is the 'Treasure hunt' game, as shown in FIG. 10d, where the game requires that the individual respond sporadically to game situations.

In the 'Treasure hunt' game, a treasure chest is presented and the individual 118 is tasked with tapping gold coins that come from the treasure chest. The game difficulty increases by increasing the time that the individual 118 has to wait before a target coin appears, and by increasing the number of times it moves in and out of the chest without stopping. In addition, the time that the coin hangs in the air is also reduced as the game level increases to ensure that the user 118 is paying attention to the task. If the user 118 misses the coin, then that level is repeated until 6 coins are successfully located.

The interaction data transmitted by the game application 318 includes identifiers that identify the individual to be assessed 118 and the game 318 being played, game situations or stimuli presented to the individual 118 during gameplay, and the individual's 118 responses to each of these stimuli.

Figure 11:
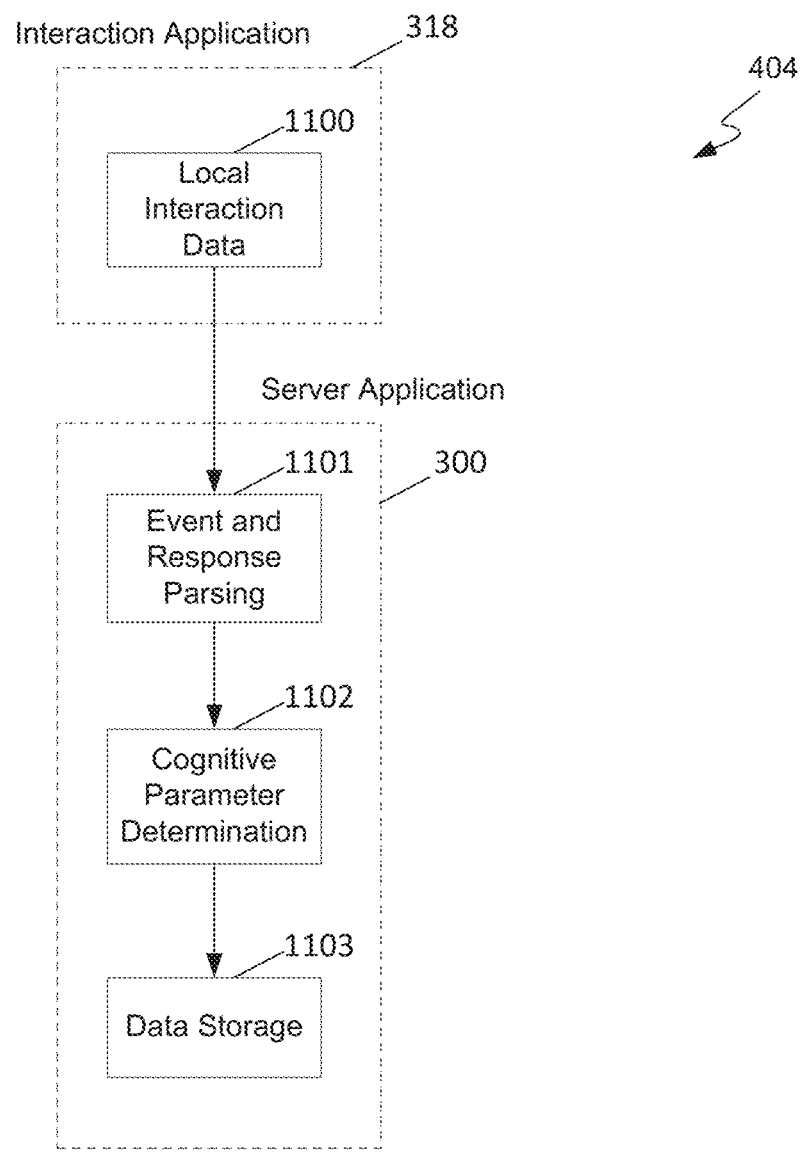
FIG. 11 is a flow diagram of a process of the cognitive assessment process of FIG. 4 for generating performance data representing quantitative measures of the performance of an individual with respect to a cognitive assessment and training application.

Assessment of an individual's cognitive performance and classification by the system 100 involves the analysis engine 304 executing a process 404, as shown in FIG. 11, for generating performance data representing quantitative measures of the performance of an individual with respect to the game application played by the individual.

In the described embodiment, the generated performance data include statistical measures or metrics of accuracy, error rate and response time. Tables 2-5 list the performance metrics generated for the games of 'Find a fish', 'Treasure hunt', 'Feed Elvis' and 'Sleepy Elvis' respectively as described above, and Table 1 lists the performance metrics common to all of these games. These metrics can be generated for sampling windows of varying sizes to produce multiple parameters for each metric type, as configured by the clinical user or researcher 120. For example, the response times of the individual 118 to respective stimuli can be measured over groups of N situation-response pairs, and an aggregated response time value can be generated by a statistical analysis of the N sample measures. The analysis engine 304 stores the generated cognitive parameters 1103 in the data repository 106.

TABLE 1

| Performance metrics common to all games | |
|---|---|
| Name | Description |
| Pos Acc | Position Accuracy, closeness to centre of target |
| Errors | Number of distractor touches per level |
| Invalids | Number of touches on the background per level |
| Hit Time | time from the last touch |
| Time/lvl | time taken to complete a level |

TABLE 1-continued

Performance metrics common to all games

| Name | Description |
|---|---|
| Hit Acc | Hit accuracy, % of valid touches per total touches |
| Attempts | No. of level attempts per game (includes retried levels) |
| Levels | No. of levels completed per game (excludes retried levels) |

TABLE 2

'Find a fish' performance metrics.

| Name | Description |
|---|---|
| Hit Acc, Color | Hit accuracy, filtered for colour levels |
| Hit Acc, Size | Hit accuracy, filtered for size levels |
| Hit Acc, Col/Size | Hit accuracy, filtered for colour & size levels |
| Hit Acc, 4 Dist | Hit accuracy, filtered for levels with 4 distractors |
| Hit Acc, 8 Dist | Hit accuracy, filtered for levels with 8 distractors |
| Hit Acc, 16 Dist | Hit accuracy, filtered for levels with 16 distractors |
| Hit Acc, 100% Dist | Hit accuracy, filtered for levels with 100% dissimilar distractors |
| Hit Acc, 75% Dist | Hit accuracy, filtered for levels with 75% dissimilar distractors |
| Hit Acc, 50% Dist | Hit accuracy, filtered for levels with 50% dissimilar distractors |
| Hit Acc, 25% Dist | Hit accuracy, filtered for levels with 25% dissimilar distractors |
| Hit Acc, 0% Dist | Hit accuracy, filtered for levels with 0% dissimilar distractors |
| Errs, Color | Errors per level, filtered for colour levels |
| Errs, Size | Errors per level, filtered for size levels |
| Errs, Col/Size | Errors per level, filtered for colour & size levels |
| Errs, 4 Dist | Errors per level, filtered for levels with 4 distractors |
| Errs, 8 Dist | Errors per level, filtered for levels with 8 distractors |
| Errs, 16 Dist | Errors per level, filtered for levels with 16 distractors |
| Errs, 100% Dist | Errors per level, filtered for levels with 100% dissimilar distractors |
| Errs, 75% Dist | Errors per level, filtered for levels with 75% dissimilar distractors |
| Errs, 50% Dist | Errors per level, filtered for levels with 50% dissimilar distractors |
| Errs, 25% Dist | Errors per level, filtered for levels with 25% dissimilar distractors |
| Errs, 0% Dist | Errors per level, filtered for levels with 0% dissimilar distractors |
| Angle | Total Angle between touches |

TABLE 3

'Treasure hunt' performance metrics.

| Name | Description |
|---|---|
| Hit Acc, Dstr Lo | Hit accuracy, filtered for levels with <12 distractors |
| Hit Acc, Dstr Hi | Hit accuracy, filtered for levels with >=12 distractors |
| Hit Acc, Dur Long | Hit accuracy, filtered for levels with a target duration >7 sec |
| Hit Acc, Dur Short | Hit accuracy, filtered for levels with target duration <=7 sec |
| Hit Acc, Time Short | Hit accuracy, filtered for levels with time between targets <=10 sec |
| Hit Acc, Time Long | Hit accuracy, filtered for levels with time between targets >10 sec |
| Errs, Dstr Lo | errors per level, filtered for levels with <12 distractors |
| Errs, Dstr Hi | errors per level, filtered for levels with >=12 distractors |
| Errs, Dur Long | errors per level, filtered for levels with a target duration >7 sec |
| Errs, Dur Short | errors per level, filtered for levels with target duration <=7 sec |
| Errs, Time Short | errors per level, filtered for levels with time between targets <=10 sec |
| Errs, Time Long | errors per level, filtered for levels with time between targets >10 sec |

TABLE 4

'Feed Elvis' performance metrics.

| Name | Description |
|---|---|
| Hit Acc, Left | hit accuracy, filtered for levels with left facing targets |
| Hit Acc, Right | hit accuracy, filtered for levels with right facing targets |
| Hit Acc, 2 fl | hit accuracy, filtered for levels with 2 flankers |
| Hit Acc, 4 fl | hit accuracy, filtered for levels with 4 flankers |
| Hit Acc, Con | hit accuracy, filtered for levels with congruent flankers |
| Hit Acc, Incon | hit accuracy, filtered for levels with incongruent flankers |
| Hit Acc, size1 | hit accuracy, filtered for levels with size 1 flankers |
| Hit Acc, size2 | hit accuracy, filtered for levels with size 2 flankers |
| Hit Acc, size3 | hit accuracy, filtered for levels with size 3 flankers |
| Hit Acc, space1 | hit accuracy, filtered for levels with space 1 flankers |
| Hit Acc, space2 | hit accuracy, filtered for levels with space 2 flankers |
| Hit Acc, space3 | hit accuracy, filtered for levels with space 3 flankers |
| Errs, Left | errors per level, filtered for levels with left facing targets |
| Errs, Right | errors per level, filtered for levels with right facing targets |
| Errs, 2 fl | errors per level, filtered for levels with 2 flankers |
| Errs, 4 fl | errors per level, filtered for levels with 4 flankers |
| Errs, Con | errors per level, filtered for levels with congruent flankers |
| Errs, Incon | errors per level, filtered for levels with incongruent flankers |
| Errs, size1 | errors per level, filtered for levels with size 1 flankers |
| Errs, size2 | errors per level, filtered for levels with size 2 flankers |
| Errs, size3 | errors per level, filtered for levels with size 3 flankers |
| Errs, space1 | errors per level, filtered for levels with space 1 flankers |
| Errs, space2 | errors per level, filtered for levels with space 2 flankers |
| Errs, space3 | errors per level, filtered for levels with space 3 flankers |

TABLE 5

'Sleepy Elvis' performance metrics.

| Name | Description |
|---|---|
| Hit Acc, Elvis | hit accuracy, filtered for levels with Elvis targets |
| Hit Acc, Lion | hit accuracy, filtered for levels with Lion targets |
| Hit Acc, 3 sec | hit accuracy, filtered for levels with a 3 sec display time |
| Hit Acc, 2 sec | hit accuracy, filtered for levels with a 2 sec display time |
| Hit Acc, Slow | hit accuracy, filtered for levels with an inter stimulus interval of 3000-4000 ms |
| Hit Acc, Med | hit accuracy, filtered for levels with an inter stimulus interval of 1800-2800 ms |
| Hit Acc, Fast | hit accuracy, filtered for levels with an inter stimulus interval of 1600 ms |
| Hit Acc, dsg 0 | hit accuracy, filtered for levels with no disguise |
| Hit Acc, dsg 1 | hit accuracy, filtered for levels with elephant ears costume |
| Hit Acc, dsg 2 | hit accuracy, filtered for levels with ears & trunk costume |

TABLE 5-continued

'Sleepy Elvis' performance metrics.

| Name | Description |
| --- | --- |
| Hit Acc, dsg 3 | hit accuracy, filtered for levels with ears, trunk, head and back piece costume |
| Hit Acc, dsg 4 | hit accuracy, filtered for levels with the entire elephant costume |
| Hit Acc, dsgTim1 | hit accuracy, filtered for levels with the disguise time = 500 ms |
| Hit Acc, dsgTim2 | hit accuracy, filtered for levels with the disguise time = 750 ms |
| Errs, Elvis | errors per level, filtered for levels with Elvis targets |
| Errs, Lion | errors per level, filtered for levels with Lion targets |
| Errs, 3 sec | errors per level, filtered for levels with a 3 sec display time |
| Errs, 2 sec | errors per level, filtered for levels with a 2 sec display time |
| Errs, Slow | errors per level, filtered for levels with an inter stimulus interval of 3000-4000 ms |
| Errs, Med | errors per level, filtered for levels with an inter stimulus interval of 1800-2800 ms |
| Errs, Fast | errors per level, filtered for levels with an inter stimulus interval of 1600 ms |
| Errs, dsg 0 | errors per level, filtered for levels with no disguise |
| Errs, dsg 1 | errors per level, filtered for levels with elephant ears costume |
| Errs, dsg 2 | errors per level, filtered for levels with ears & trunk costume |
| Errs, dsg 3 | errors per level, filtered for levels with ears, trunk, head and back piece costume |
| Errs, dsg 4 | errors per level, filtered for levels with the entire elephant costume |
| Errs, dsgTim1 | errors per level, filtered for levels with the disguise time = 500 ms |
| Errs, dsgTim2 | errors per level, filtered for levels with the disguise time = 750 ms |

Figure 12:
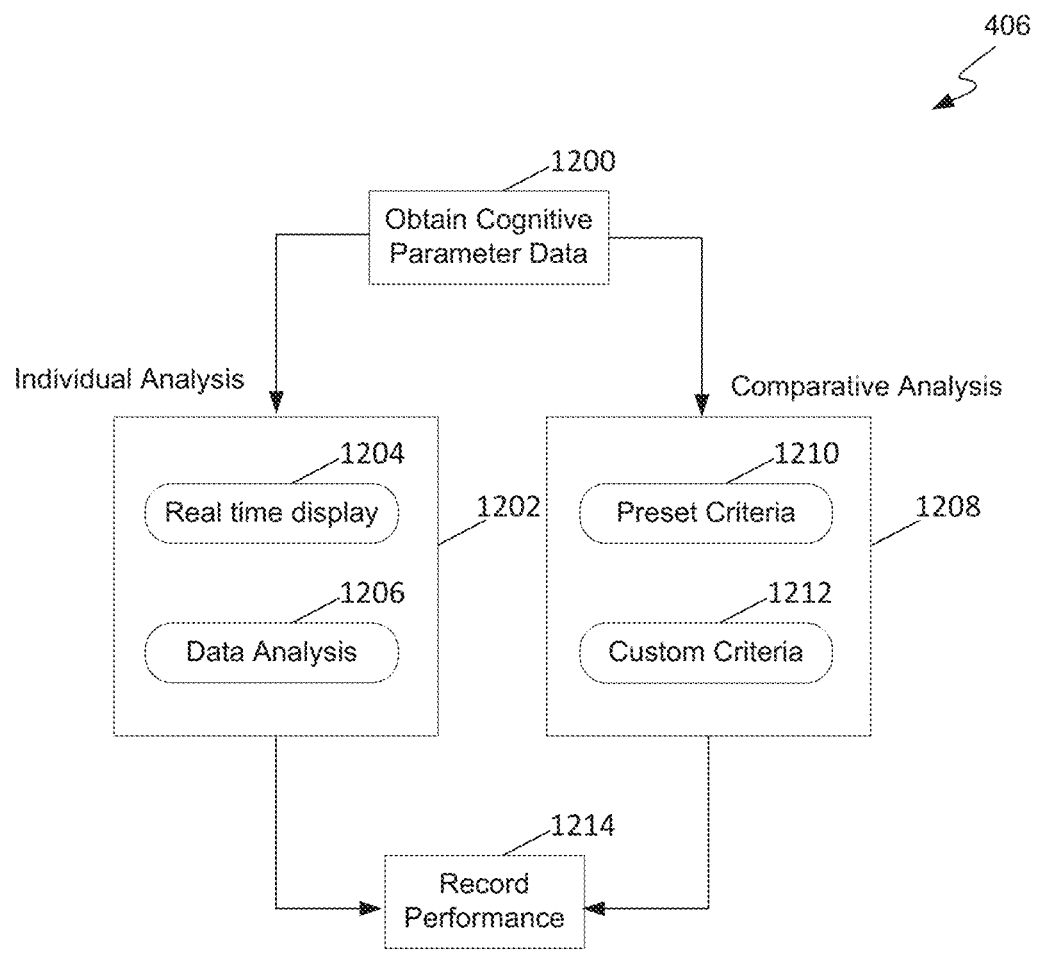
FIG. 12 is a flow diagram of a process of the cognitive assessment process of FIG. 4 for generating classification data indicative of at least one cognitive classification for the individual.

In the described embodiment, the cognitive assessment system 100 stores a new set of performance data for each individual 118, each time that the individual 118 plays a game 318 on the interaction device 114. Assessments of cognitive performance involve the analysis of these sets of parameter data using an analysis process 1200 to generate representations of performance, as shown in FIG. 12.

To assess a selected aspect of cognitive performance of a selected individual at a selected time, the analysis engine 304 obtains the corresponding set of performance data from the data repository 106. For example, the clinical user or researcher 120 might choose to assess cognitive performance based on a specific game type as determined by the individual's condition, and/or over a selected time interval of cognitive ability measurement (such as any time in the last 6 months). Using the resulting sets of cognitive parameter data, a selected individual analysis process 1202 is applied to assess the cognitive performance of the individual 118. The individual analysis process 1202 can choose to assess the cognitive performance of the individual in isolation, or to apply one or more data analysis 1206 techniques, including statistical analysis, regression, and/or clustering, to produce an assessment of the individual's cognitive performance relative to other individuals. For example, where clustering analysis is used as a classification or diagnosis tool, the closeness of the individual to each other cluster of other individuals in an N-dimensional space of selected performance metrics can be assessed by determining the distance between the N-dimensional vector of performance metric values for that individual and the average N-dimensional vector representing the centroid of the cluster. Where the individuals of a cluster have a common developmental disability diagnosis, the classification(s) or diagnosis/diagnoses of the assessed individual can be assessed (and expressed mathematically) in terms of these distances, or as a provisional diagnosis where the performance metrics of an individual appear to belong to a cluster of individuals with a common known diagnosis.

Figure 13:
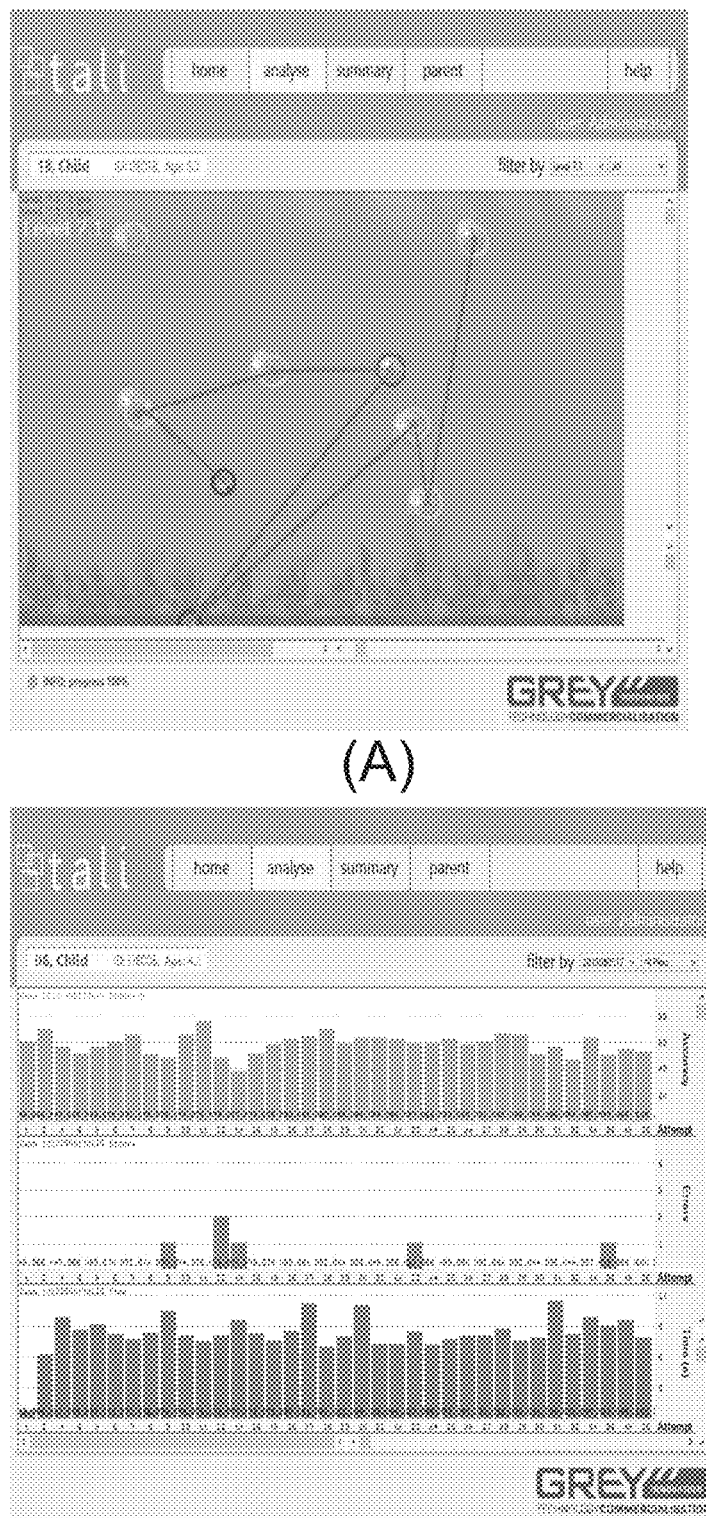
FIG. 13a is a screenshot of a user interaction playback display of the cognitive assessment and training system, showing the sequence of individual actions of an individual interacting with a cognitive assessment and training application.
FIG. 13b is a screenshot of an interaction statistics display generated by the cognitive assessment and training system, showing the performance of the individual as a function of time during interaction with a cognitive assessment and training application.

The cognitive assessment system 100 allows the clinical user or researcher 120 to customise the methods used to perform the cognitive analysis process 1202. The clinical user 120 can manually analyse the performance of an individual by viewing a second-by-second real-time display 1204 of the individual's game play. For example, FIG. 13a shows a screenshot representing the sequence of actions taken by an individual's while playing a selected portion of a selective attention game, allowing the clinician to observe the individuals interactions and decisions. The clinical user 120 can also choose to simultaneously view all or a subset of multiple performance metrics of the individual, as shown in FIG. 13b. Additionally, the clinical user 120 can conduct a multidimensional data analysis to view correlations between the different performance metrics for the individual, for the purpose of determining or providing an indication of a possible classification of the individual with respect to one or more developmental disability classifications or diagnoses.

The performance determination step 406 can also involve a comparative analysis process 1208 to assess the performance of the given individual 118 in comparison to a selected control group of other individuals, or to a representation of a known condition. The clinical user 120 can choose to use preset criteria 1210, such as game type or condition, to perform the comparative analysis, where the analysis involves the determination of statistical differences between the performance metrics of the given individual and one or more control sets of performance metrics for other groups of individuals (e.g., including groups of individuals having different types or degrees of developmental disabilities, and a group of individuals without any developmental disability). Alternatively, custom criteria can be selected at step 1212 for the comparison, such as the selection of specific performance metrics. The control group can be varied by the application of filters including development disability condition, gender, and age.

Figure 14:
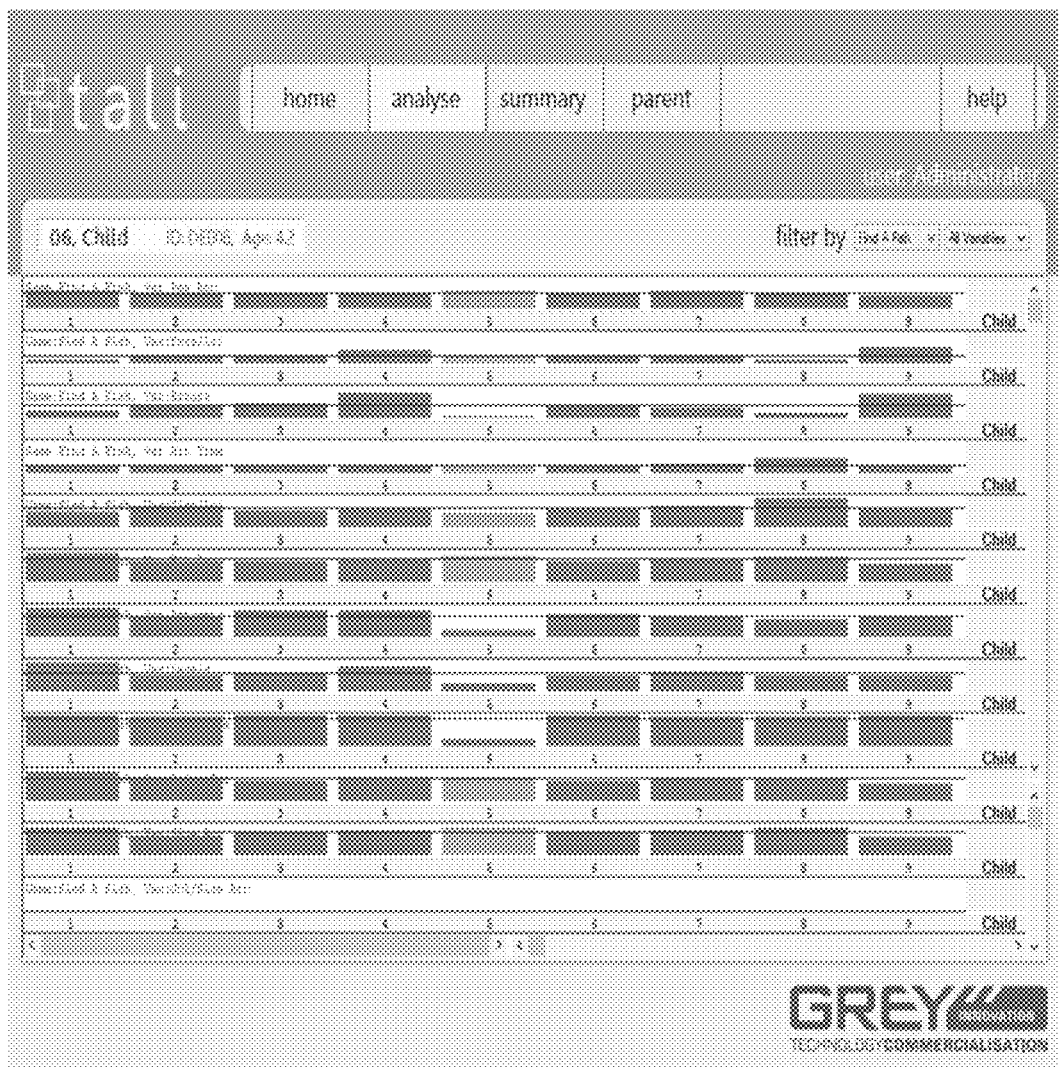
FIG. 14 is a screenshot of a user analysis display generated by the cognitive assessment and training system, showing the interaction performance of an individual over a series of sessions with a selected cognitive assessment and training application, and highlighting statistically significant deviations from the interaction performance of a corresponding selected reference population of users.
Figure 20:
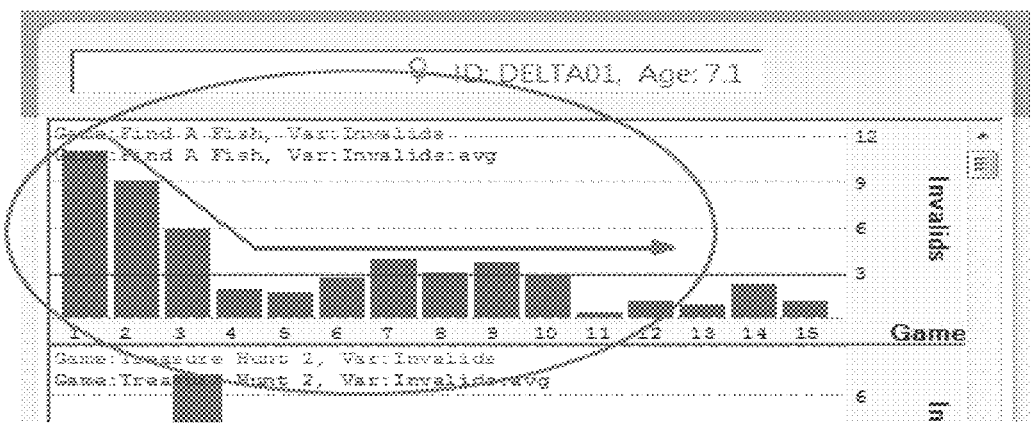
FIG. 20 is a partial screenshot of a graphical representation of the total number of invalid touch events made by the individual during a game for successive gameplays by the individual, showing a reduction in the number of 'invalids' (invalid touch events) over time as the individual learns the game and improves their performance.
Figure 21:
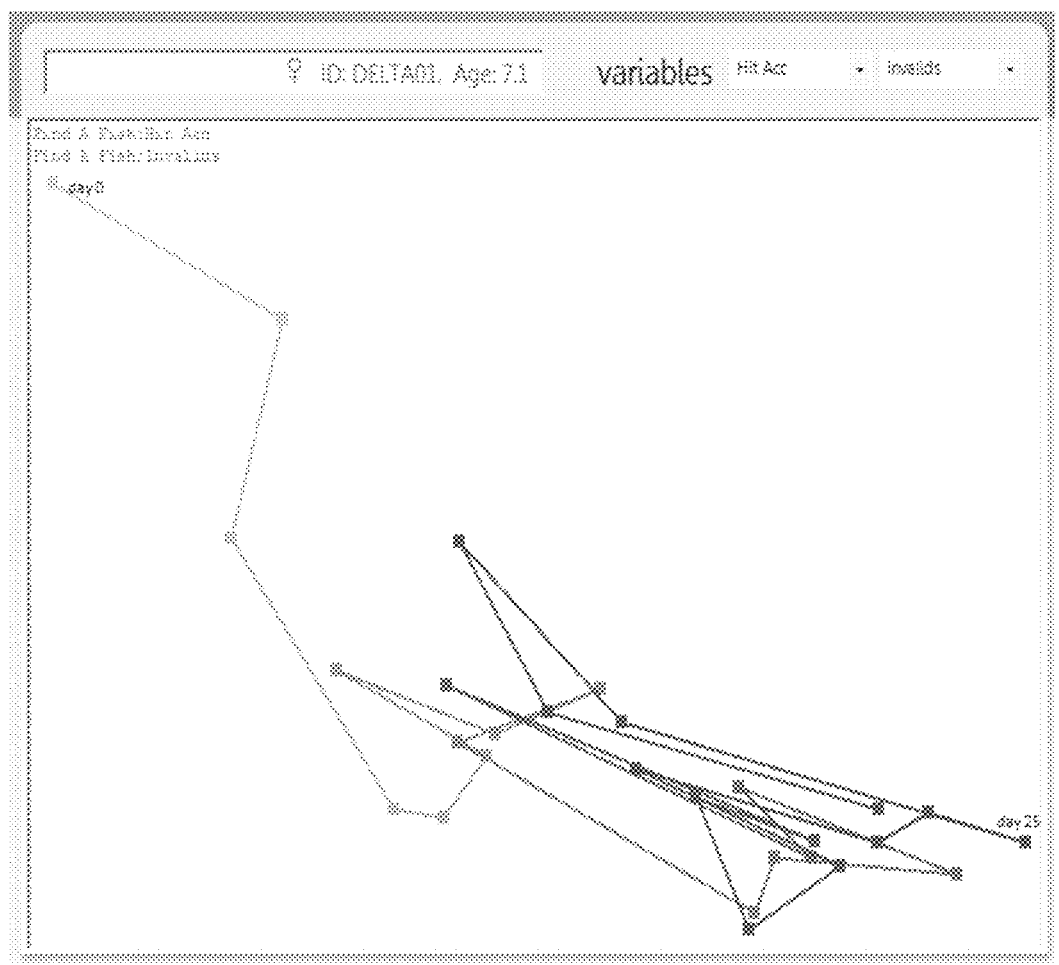
FIG. 21 is a partial screenshot of a graphical representation of the relationship between user-selected quantitative measures of the performance of an individual (in this example, the measures being 'hit accuracy' on the x-axis and 'invalids' (invalid touch events) on the y-axis) while playing the Find a Fish game from day 0 to day 25 of a training program, demonstrating a significant reduction in the number of invalids and a corresponding increase in hit accuracy as the individual improves their performance over a series of training sessions.

The cognitive assessment system 100 provides the clinical user 120 with a visual display of the comparative analysis, as shown in FIG. 14. The user 120 can select to highlight in a selected colour performance metrics that lie within (or conversely outside) 1.5 standard deviations of a reference data set of performance metrics for other individuals assessed by the system 100. The clinical user 120 is thus alerted to extreme differences in the parameter values of the cognitive data for the given individual 118 compared to those of the control set. Other visualisations can be used to assess other aspects of an individual's performance over time. For example, FIG. 20 is a screenshot illustrating the number of invalid touch events made by an individual during the course of gameplay of the Find A Fish game, showing a decrease in error rate to a relatively constant rate as the individual learns the game and thus improves in performance.

In the described embodiments, the cognitive performance of an individual is represented as a statistical model, where the model parameters are determined by the analysis engine 304 and are subsequently stored in the data repository 106 at step 1214. Analysis can also be performed automatically by the analysis engine 304 in accordance with configuration options set by the clinical user 120 for the given individual 118 when required, according to the predetermined schedule, or when specifically requested by a clinical user 120 with appropriate authority. In practice, it has been found that of all the performance metrics described herein, only about 12 of them are required in order to characterise about 95% of the disability characteristic behaviours of children assessed by the system 100, and are thus sufficient to represent a "model" of a child being assessed, and to compare with models of other children as described herein.

Figure 15:
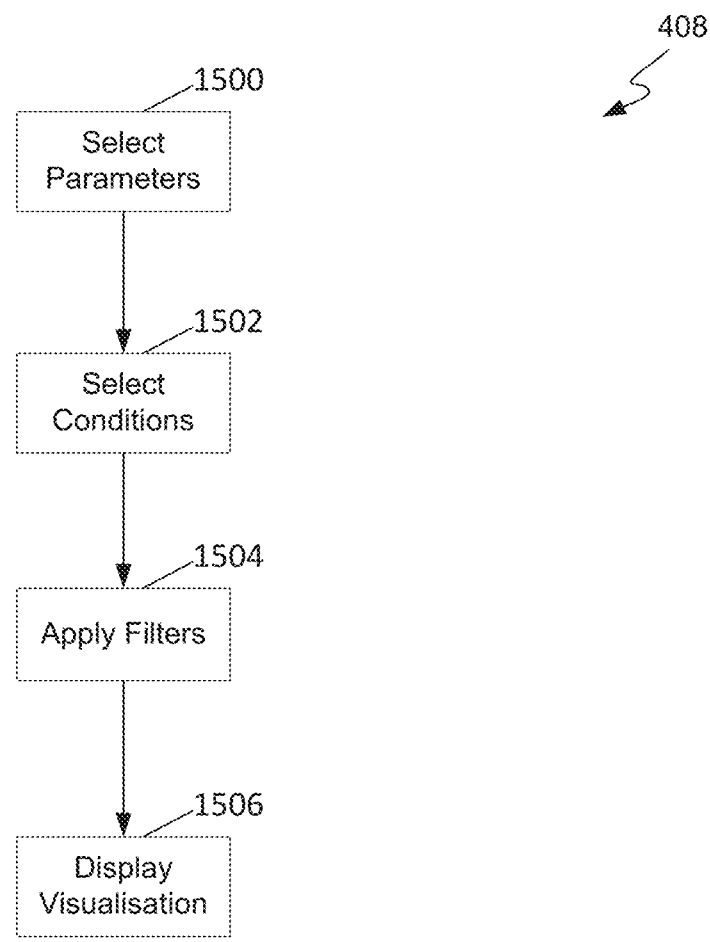
FIG. 15 is a flow diagram of an interaction performance visualisation process of the cognitive assessment and training system.

A clinical user or researcher 120 can visualise the cognitive performance data 408 of one or more selected individuals assessed by the system 100 using the visualisation process 1506 shown in FIG. 15. The clinical user 120 is presented with a graphical user interface (GUI) that allows the selection of one or more performance metrics (or 'cognitive parameters') 1500 to be visualised. The visualisation illustrates the relationships between performance parameters. One or more developmental disability conditions can be selected by the clinical user 120 at step 1502, which causes the visualisation process 1506 to limit the displayed data to data associated with individuals affected by the selected condition(s). Multivariate filtering and analysis methods can be applied at step 1504, as selected by the clinical user or researcher 102, from a set of available analysis methods, including principal component analysis (PCA) clustering techniques, support vector machines, Bayesian analysis, decision trees, and genetic algorithms in order to identify and quantify correlations between one or more of the performance metrics and corresponding characteristics or disability classifications of assessed individuals. The clinical user or researcher 120 can thus develop arbitrary associations between performance metrics that provide the desired ability to discriminate between individuals or developmental disability conditions of interest. This can also be performed automatically by selecting a population of individuals based on selection criteria entered by the clinical user or researcher 120, and then automatically processing the resulting sets of performance metrics in order to select a subset of these performance metrics that provides the best predictive capability within the selected population, based on known diagnoses and/or other characteristics of the individuals. Once identified, the selected subset of performance metrics can then be used to assess an unknown individual.

Figure 16:
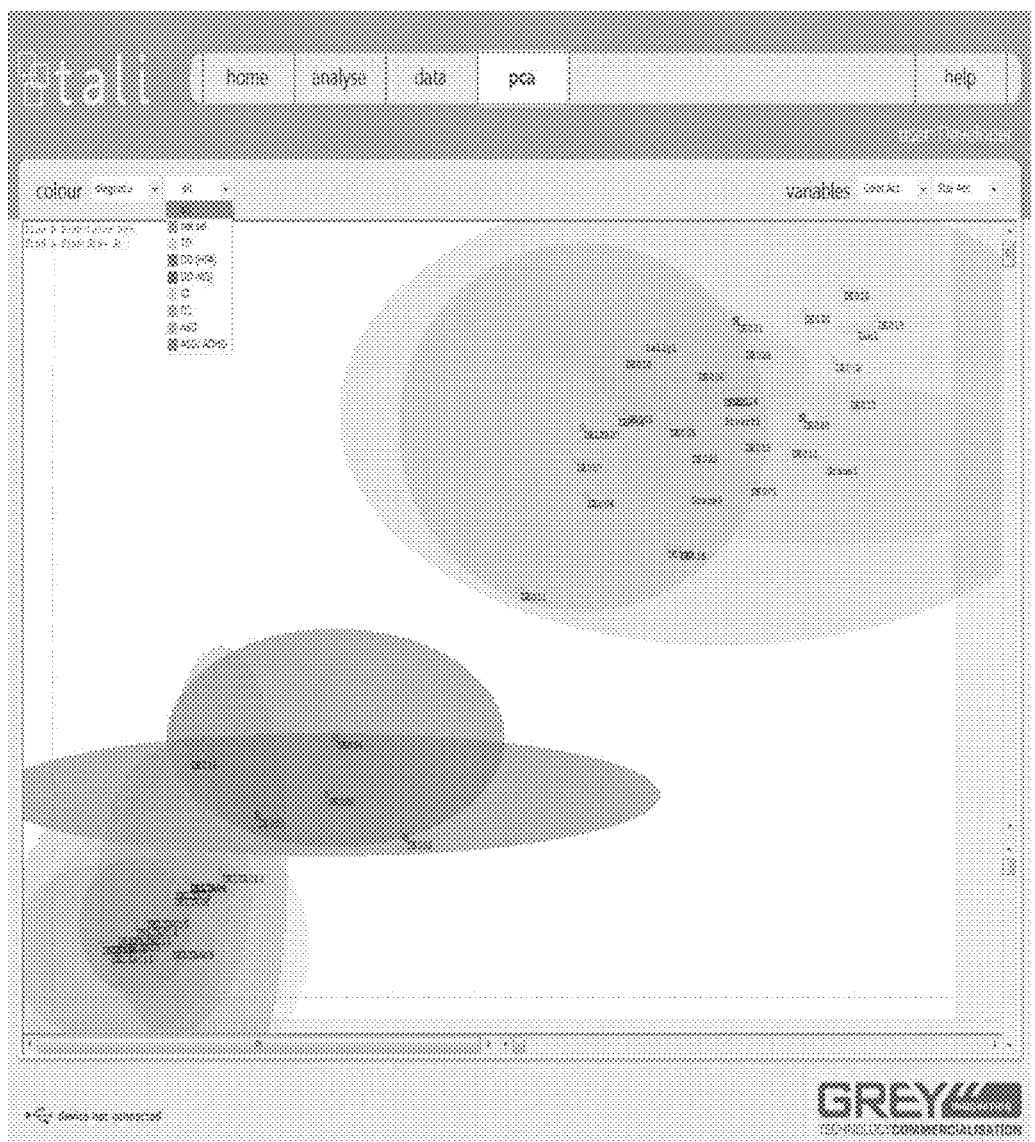
FIG. 16 is a flow diagram of a display generated by the cognitive assessment and training system, showing clustering of the interaction performance of individuals with corresponding developmental difficulties with respect to multiple interaction performance parameters measured by the cognitive assessment system.

FIG. 16 shows an example of the visualisation data 1506 generated from two selected parameters (performance metrics). Statistical parameter distributions are shown for each individual colour-coded according to the diagnosis of the individual (if known), assisting the clinician to gauge how effectively the performance metrics distinguish between different diagnosis conditions such as high functioning autism, low functioning autism, downs syndrome, and neurotypical development. The parameter associations identified by the visualisation process can be stored in the data repository 106, if desired. The customised parameter sets can then be used to modify the analysis process 410 via the creation of new statistical models that improve the accuracy of the performance determination process 406.

Figure 17:
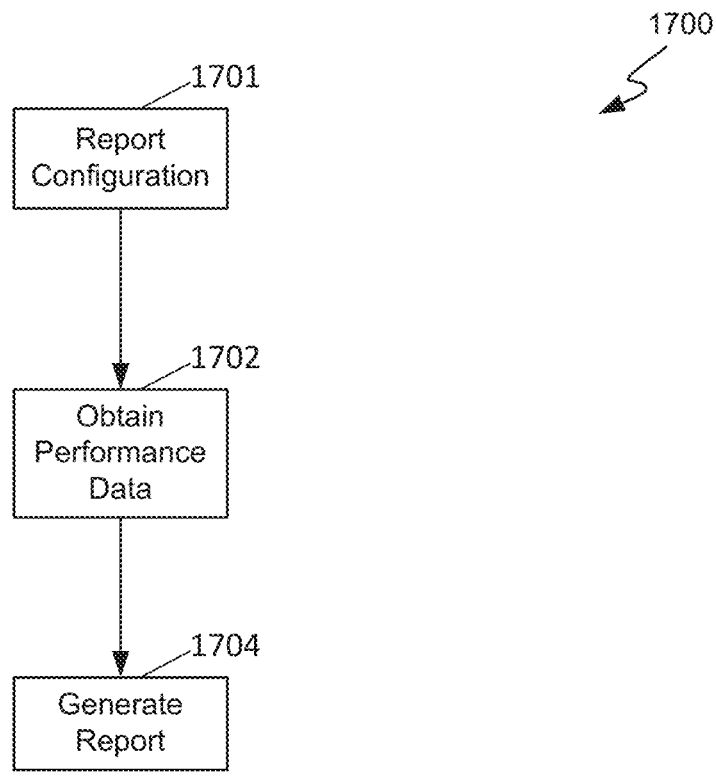
FIG. 17 is a flow diagram of a report generation process of the cognitive assessment process of FIG. 4.

The cognitive assessment system 100 includes a reporting component 108 that executes a report generation process 1700, as shown in FIG. 17, to generate reports 412 summarising the cognitive performance of individuals 118. The report generation 1700 involves a report configuration step 1701 that allows a user to select the type of report produced, the frequency at which reports are automatically generated, and the set of clinical users 120 who will receive the report. Each report is specific to an assessed individual 118, and generation of the report involves obtaining the relevant performance data 1702 from the data repository 106. In the described embodiment, performance data summarised within the report includes individual and comparative analysis models. For example, a report can show the performance of the individual 118 according to: i) absolute statistical measures of cognitive performance; and ii) a comparative ranking of their general (or parameter specific) performance compared to a control group, such as other individuals with the same condition. The reported performance may include the exact cognitive performance metrics determined by the system 100, but may also include other information inferred from those performance metrics.

Figure 18:
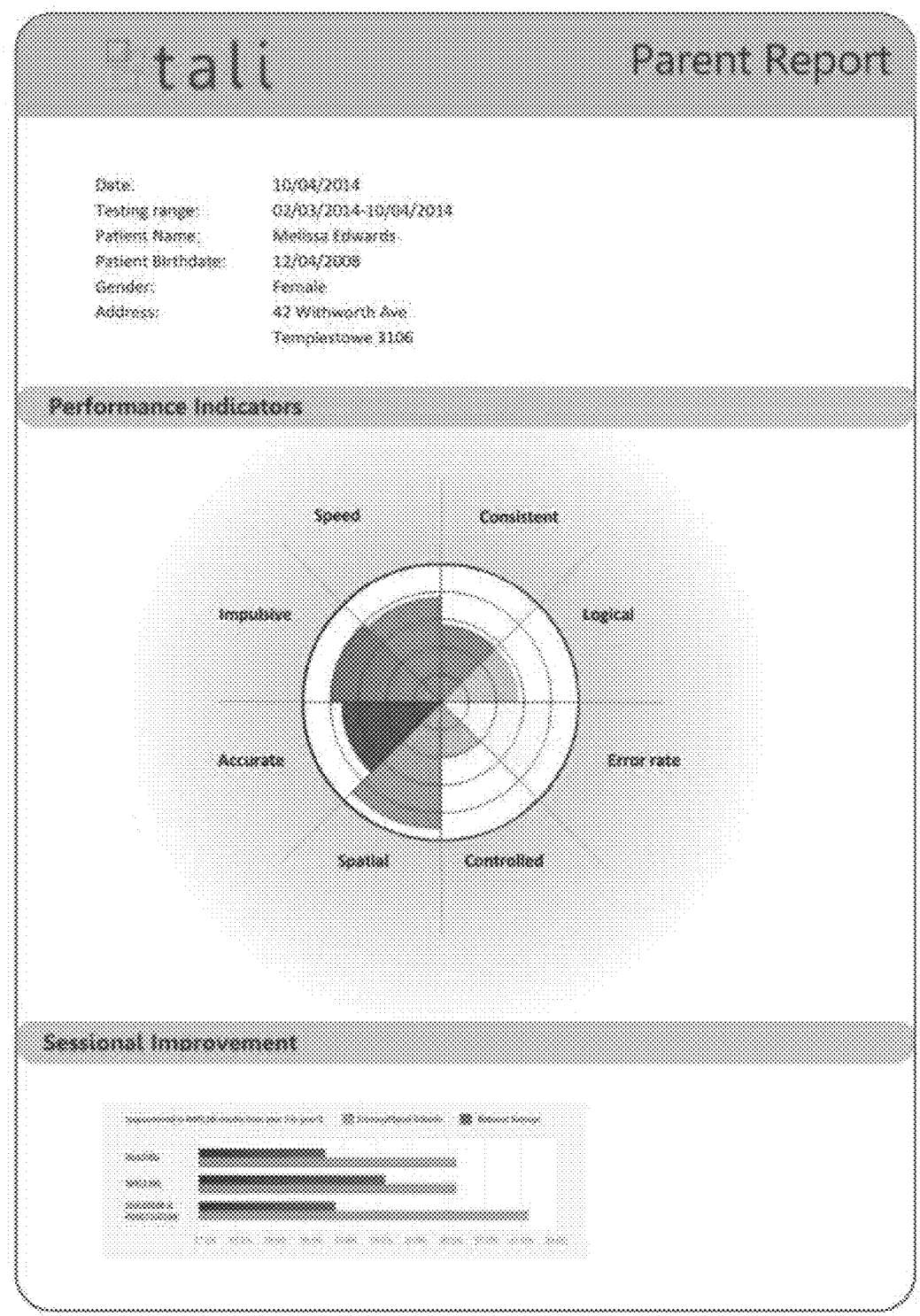
FIG. 18 is a screenshot of an example report display generated by the report generation process of FIG. 17, showing an individual's eight performance indicators in the form of a spider plot, and the improvement in the individual's performance over several sessions of gameplay using the cognitive assessment system.

The report generation process 1704 for an assessed user 118 varies based on the recipient of the report. For example, reports generated for the medical practitioner of an individual 118 can contain additional details, such as clinical notes, which are omitted from reports generated for the parent or guardian of the assessed individual. FIG. 18 shows an example report for a parent of an assessed individual, where the report contains metrics derived from the cognitive performance model of the individual 118. The format and content of the report can be customised by clinical users 120 in order to allow the analysis provided by the system to remain consistent with developments in the field.

Reports can be generated automatically by the system 100 at regular intervals using cognitive performance and/or parameter data between the present time and the time of the last generated report for the same user 120 and assessed individual 118. The time interval of reporting can be specified by a clinical user 120 for each individual. The periodic generation of reports enables the progress of an individual 118 to be tracked against the wider population, and allows the assessment of developmental conditions to be continually improved as more data is made available to the system 100. Additionally, a clinician 120 can request a report for a specific individual 118 whom they have treated, and the system can output an immediate performance report based using the time interval indicated by the clinician 120.

In addition to its ability to quantitatively assess individuals for characteristics or diagnoses of developmental disabilities, the system 100 is also an effective tool for training individuals in order to improve their cognitive abilities, in particular deficits in attention-based abilities.

In order to demonstrate the applicability of the system 100 in assessing attention-based abilities of individuals with developmental disabilities, nine children with developmental disabilities ($M_{age}$=8 years, 5 months) and their parents took part in a focus group which involved using the program and then providing feedback on their experience. In order to assess the construct validity and sensitivity of the program, 90 typically developing children ($M_{age}$=4 years 4 months, 3 years to 5 years) were recruited. The system 100 acquired interaction data for the participants, and this was used to generate corresponding performance metrics as described above. In addition, two standard measures of attention were also applied to the participants, namely Wilding Attention Tasks ("WATT") and the Kiddie Continuous Performance Task ("K-CPT").

Qualitative data demonstrated that children with a developmental disability were able to engage with the game applications described above and understand the task requirements. As shown in Table 6 below, correlation coefficients revealed significant positive correlations between standard measures of attention and the performance metrics of the system 100 relating to selective attention tasks, $r (85)=0.48$, $p<0.001$, cognitive flexibility tasks, $r (86)=0.44$, $p<0.001$, sustained attention tasks, $r (84)=0.36$, $p<0.001$, and response inhibition tasks, $r (84)=0.47$, $p<0.001$.

A series of hierarchical multiple regression analyses were used to predict performance on each of the system 100 tasks. For each of the game application tasks, the addition of age as a parameter significantly improved the prediction. In combination, the two predictor variables of age and gender explained 40% of the variance in selective attention performance [adjusted $R^2=0.386$, $F(2, 87)=28.96$, $p<0.001$], 12.3% of the variance in sustained attention performance, [adjusted $R^2=0.103$, $F(2, 87)=6.102$, $p=0.003$], 31.3% of the variance in cognitive flexibility performance, [adjusted $R^2=0.298$, $F(2, 87)=19.846$, $p<0.001$] and 11.8% of the variance in response inhibition performance [adjusted $R^2=0.098$, $F(2, 87)=5.847$, $p=0.004$].

TABLE 6

Correlations between errors on the system 100 subtests and standard measures of attention

| performance metric generated by the system 100 | Standard Attentional Measures | | |
|---|---|---|---|
| | VISEARCH Single Search | K-CPT | VISEARCH Dual Search |
| Selection | .480*** | .380*** | .431*** |
| Vigilance | .439*** | .360*** | .259* |
| Conflict Resolution | .524*** | .509*** | .441*** |
| Response Inhibition | .421*** | .467*** | .456*** |

To demonstrate the sensitivity of the cognitive assessment and training system and process in detecting age-related changes in attention performance, a one way ANOVA was conducted to assess differences in performance across age ranges. Significant differences across ages were found for all tasks: selective attention ($p=0.01$); sustained attention ($p=0.03$), conflict resolution ($p=0.01$) and response inhibition ($p=0.01$).

A training program in the form of a double blind randomized controlled trial was conducted. 80 children with intellectual disabilities ($M_{age}=8.02$, range 4 to 10 years, IQ<75) were randomly assigned to an adaptive attention training program using the system 100 (intervention) or a non-adaptive control program. As described above, the game applications used for the program incorporated selective attention, sustained attention and attentional control tasks. The intervention ran for 5 weeks and consisted of 25 sessions, lasting 20 minutes each. Children were assessed on a range of standardised and tailored assessments before the intervention, immediately after the intervention and 3 months after the intervention. Both parent and teacher reports of inattentive behaviour were obtained.

For the intervention group, repeated measures ANOVAs revealed significant main effects of time for all of the cognitive attention variables: feature search errors, $F(2, 74)=11.09$, $p=0.001$; feature search time, $F(2, 74)=3.20$, $p=0.05$; conjunction search errors, $(2, 62)=14.61$, $p=0.001$; conjunction search time, $F(2,64)=5.59$, $p=0.006$; vigilance targets, $F(2, 70)=9.11$, $p=0.001$; and vigilance errors, $F(2, 70)=4.52$, $p=0.014$. Post hoc pairwise comparisons with Bonferroni adjustment revealed that the intervention group made significantly fewer errors on the feature search and conjunction search tasks across the trial. In addition, the time taken to complete the conjunction search task was shown to significantly decrease from $T_1$ to $T_2$ ($p=0.03$). In terms of the vigilance task, improvements were present at $T_3$ when compared to $T_1$ for both targets located ($p=0.002$) and errors made ($p=0.02$). In contrast, improvements were not as readily observed in the control group, with significant main effects of time only being present for one variable; time taken to complete the conjunction search task, $F(2,68)=6.46$, $p=0.003$. Pairwise comparisons revealed that marginally statistically significant improvements were seen from $T_1$ to $T_2$ ($p=0.05$) which were maintained up until $T_3$ ($p=0.03$).

In order to assess treatment effects on the magnitude of improvements in attention skills across time, repeated measures ANOVAs were conducted with condition (Intervention or Control) as the between subjects variable and time as the independent variable. Significant interactions were observed for both feature search errors and conjunction search errors, indicating that the reduction in errors made over time differed significantly across groups. Post hoc tests between subjects contrast for time showed that at $T_1$ participants in the intervention group made significantly more errors when compared to the control group on both the feature search, $F(1, 74)=4.14$, $p=0.05$ and conjunction search task, $F(1, 69)=3.93$, $p=0.05$. However by $T_2$ there was no difference across groups on either of the search tasks ($p>0.05$), with the intervention group reducing the amount of errors they made. These improvements were maintained up till $T_3$, as no differences across groups were present ($p>0.05$). No other interaction effects of time and group were observed for the additional attention variables.

Paired-samples t tests revealed that children in the intervention group showed significant improvements in performance on complex selective attention tasks immediately after training, ($t(15)=-3.25$, $p<0.01$). Although improvements were not observed in other attentional processes immediately after training, improvements in basic selective attention ($t(15)=-2.85$, $p<0.05$) and sustained attention ($t(15)=-2.20$, $p<0.05$) were evident at the 3 month follow up. No improvements were observed in the control group on any attention task, either immediately after training or at follow up. Behavioural measures of inattentive and hyperactive behaviour completed by parents and teachers indicated improvements in the intervention group after training, however these improvements did not reach significance.

The targeted intervention provided by the system 100 produced improvements in core attentional processes in children with developmental disabilities when compared to the control program. Importantly, these preliminary results emphasise the potential of these training paradigms, and offer an alternative to pharmaceutical interventions in individuals who are 'at risk' or already vulnerable to attention difficulties.

Many modifications will be apparent to those skilled in the art without departing from the scope of the present invention.

The invention claimed is:

1. A process for cognitive assessment and training, the process being executed by at least one processor of a computing system, and comprising:
   receiving interaction data representing interactions between an application executing on an electronic device and an individual interacting with the executing application;
   processing the interaction data to generate performance data representing quantitative measures of the performance of the individual with respect to the executing application;
   generating display data representing a visualisation of one or more quantitative measures of performance of the individual and one or more corresponding quantitative measures of performance of one or more other assessed individuals;

receiving an input representing an analysis process modified by a user based on the visualisation;

in response to the input from the user, customising operations of parameters that influence a determination of the cognitive performance or classifications of one or more other assessed individuals; and performing the customised operations for the performance data for the individual to generate a desired cognitive assessment and training data indicative of at least one attention-related ability of the individual.

2. The process of claim 1, wherein the application is a game, and the interaction data represents interactions between the game and the individual playing the game, the game being configured to improve attention-related abilities of the individual.

3. The process of claim 1, wherein the quantitative measures of the performance of the individual with respect to the executing application include quantitative measures of accuracy, error rate, and response time.

4. The process of claim 1, wherein the step of processing the performance data includes processing the performance data for the individual and corresponding performance data for one or more other individuals having one or more cognitive ability classifications, including a neurotypical classification and/or one or more developmental disability classifications, the cognitive assessment and training data being indicative of a classification of the individual with respect to the one or more cognitive ability classifications.

5. The process of claim 4, wherein the generated display data further represents a visualisation of the cognitive assessment and training data of the individual and the one or more cognitive ability classifications of the one or more other individuals.

6. The process of claim 5, wherein the visualisation allows the user to compare the performance of the individual to the corresponding performance of the other individuals.

7. The process of claim 6, wherein the visualisation includes an interactive control for selecting the one or more quantitative measures of performance for display to the user.

8. The process of claim 4, wherein the one or more other individuals have one or more cognitive ability classifications selected by a user from a set of cognitive ability classifications.

9. The process of claim 5, wherein the visualisation is configured to visually differentiate any quantitative measures of performance of the individual that differ significantly from the corresponding quantitative measures of performance for the other individuals.

10. A computer program product for cognitive assessment and training of an individual, including executable instructions that, when executed by at least one processor of a computing system, performs the process of claim 1.

11. A cognitive assessment and training system, including:
a random access memory;
at least one processor;
a display to display application content to a user of the system;
at least one input device to receive input from the individual;
wherein the system is configured to execute the process of claim 1.

12. The cognitive assessment and training system of claim 11, wherein the system is a tablet computer and the display and input device are components of a touchscreen of the tablet computer.

13. The process of claim 1, wherein the customised operations include at least one of the acts of:
performing a filtering and analysis operation on the quantitative measures;
selecting one or more individuals as the assessed and trained individuals; and
selecting one or more attention-related abilities to limit the displayed data to data associated with assessed and trained individuals affected by the selected abilities.

14. The process of claim 13, wherein the customised operations include the performing the filtering and analysis operation, the filtering and analysis operation involves a multivariate analysis procedure that includes performing at least one of a principal component analysis and a clustering process.

15. The process of claim 1, wherein the customised operations include developing an arbitrary relationship of parameters between quantitative measures associated with performance for the at least one assessed individual and the at least one trained individual so as to discriminate between the attention-related abilities of these individuals.

16. A process for assessing and training cognitive or attentional performance of an individual, the process being executed by at least one processor of a computing system and comprising:
displaying a plurality of visual stimuli on a display of the computing system;
receiving inputs of an individual using the computing system, the inputs being responsive to the displayed visual stimuli;
generating interaction data representing the visual stimuli and the corresponding inputs of the individual; and
sending the interaction data to a data processing system configured to:
(i) process the interaction data to generate performance data representing quantitative measures of the performance of the individual with respect to the visual stimuli; and
(ii) generate cognitive assessment data indicative of at least one attention-related ability of the individual, wherein the generation of the cognitive assessment data is based on customised operations in response to an input representing an analysis process modified by a user, and
wherein, in response to the generation of display data representing a visualisation of one or more of the quantitative measures of performance of the individual, and one or more corresponding quantitative measures of performance for one or more other assessed individuals, the user provides an input to the at least one processor for modifying the analysis process, and
wherein the at least one processor performs, in response to the input, customised operations of parameters that influence a determination of the cognitive performance or classifications of the one or more other assessed individuals, so that desired cognitive assessment and training data indicative of at least one attention-related ability of the individual are generated.

17. The process of claim 16, wherein the visual stimuli represent a game being played by the individual, the visual stimuli being configured for assessing and training attention-related abilities of the individual.

18. A method for cognitive assessment and training of an individual, including:
providing cognitive training sessions in which the individual continuously interacts with a cognitive assessment and training system for at least a predetermined period of time, the cognitive assessment and training system being configured to execute the process of claim 16, wherein the executing process implements a computer game being played by the individual, and the computer game is configured to train attention-related abilities of the individual playing the game; and the step of processing the interaction data is performed at least before and after the cognitive training sessions to assess improvements in one or more of the attention-related abilities of the individual.

19. A process for assessing and training cognitive or attentional performance of an individual, the process being executed by at least one processor of a computing system and including:

displaying a plurality of visual stimuli on a display of the computing system;

receiving inputs of an individual using the computing system responsive to the displayed visual stimuli;

generating interaction data representing the visual stimuli and the corresponding inputs of the individual;

processing the interaction data to generate performance data representing quantitative measures of the performance of the individual with respect to the visual stimuli; and generating cognitive assessment data indicative of at least one attention-related ability of the individual, the generating of the cognitive assessment data being based on customised operations in response to an input representing an analysis process modified by a user, wherein the analysis process is modified in response to the generation of display data representing a visualisation of one or more of the quantitative measures of performance of the individual, and one or more corresponding quantitative measures of performance for one or more other assessed individuals; and wherein the customised operations include one or more operations that influence a determination of the cognitive performance or classifications of the individual in respect of the one or more other assessed individuals based on their respective quantitative measures of performance.

\* \* \* \* \*